United States Patent [19]

Wong et al.

[11] Patent Number: 5,276,120

[45] Date of Patent: Jan. 4, 1994

[54] PROCESS FOR FORMING OMEGA-DEUXY-AZASUGARS

[75] Inventors: Chi-Huey Wong, Rancho Santa Fe, Calif.; Tetsuya Kajimoto, Kumamoto, Japan; Kun-Chin Liu; Lihren Chen, both of San Diego, Calif.

[73] Assignee: The Scripps Research Institute, La Jolla, Calif.

[21] Appl. No.: 835,237

[22] Filed: Feb. 13, 1992

Related U.S. Application Data

[63] Continuation-in-part of Ser. No. 707,600, May 30, 1991, abandoned.

[51] Int. Cl.$^5$ .................. C07D 211/40; C07D 207/12
[52] U.S. Cl. .................... 546/184; 546/242; 548/541
[58] Field of Search ................ 546/184, 242; 548/541

[56] References Cited

U.S. PATENT DOCUMENTS 5,017,704  5/1991  Fleet et al. ..................... 546/242
5,100,797  3/1992  Fleet et al. ..................... 435/200

OTHER PUBLICATIONS

Liebs. Ann. Chem.; 1989; 423–428; Schmidt et al.
Paulsen et al., *Adv. Carbohydr. Chem.* 1968, 23, 115.
Fellows, *Chem. Br.* 1987, 23, 842.
Truscheit et al., *Angew. Chem. Int. Ed. Engl.* 1981, 20, 744.
Inouye et al., *Tetrahedron* 1968, 24, 2125.
Müller, in *Biotechnology*, Rehm, H.-J. et al., eds., VCH Verlagsgesellschaft Weinheim 1985, vol. 4, Chap. 18.
Liu, *J. Org. Chem.* 1987, 52, 4717.
Anzeveno et al., *J. Org. Chem.* 1989, 54, 2539.
Yoshikuni et al., *J. Pharmacobio-Dyn* 1988, 111, 356.
Karpas et al., *Proc. Natl. Acad. Sci.* 1988, 85, 9229.
Walker et al., *Proc. Natl. Acad. Sci.* 1987, 84, 8120.
Winkler et al., *J. Med. Chem.* 1989, 32, 2084.
Humphries, M. J., et al. *Cancer Res.* 1986, 46, 5215.
Fleet, *Chem. Br.* 1989, 25, 287.
Bernotas et al., *Tetrahedron Lett.* 1985, 26, 1123.
Setoi et al., *Chem. Pharm. Bull.* 1986, 34, 2642.
Legler et al., *Carbohydr. Res.* 1984, 128, 61.
Hanesian, *Chem. Ind.* 1966, 2126.
Ziegler et al., *Angew Chem. Int. Ed. Engl.* 1988, 29, 716.
Buchanan et al., *J. Chem. Soc. Perkin Trans.* 1990, 699.
Fleet et al., *J. Chem. Soc. Perkin Trans.* 1989, 665.
Dondoni et al., *J. Chem. Soc. Chem. Commun.* 1990, 854.
Fleet et al., *Chem. Lett.* 1986, 1051.
Ciufolini et al., *J. Am. Chem. Soc.* 1989, 111, 3473.
Vasella et al., *Helv. Chim. Acta.* 1982 65, 1134.
Daigo et al., *Chem. Pharm. Bull.* 1986, 34, 2243.
Fellows et al., *J. C. S. Chem. Comm.* 1979, 977.
Saul et al. *Arch. Biochem. Biophys.* 1983, 221, 593.
Paulsen et al., *Chem. Ber.* 1967, 100, 802.
Saeki et al., *Chem. Pharm. Bull.* 1968, 16, 2477.
Kinast et al., *Angew. Chem. Int. Ed. Engl.* 1981, 20, 805.
Bernotas et al., *Tetrahedron Lett.* 1984, 25, 165.
Iida, *J. Org. Chem.* 1987, 52, 3337.

(List continued on next page.)

*Primary Examiner*—Marianne M. Cintins
*Assistant Examiner*—Michael B. Hydorn
*Attorney, Agent, or Firm*—Dressler, Goldsmith, Shore, Sutker & Milnamow

[57] ABSTRACT

A process for the preparation of a 1,5-dideoxy-yazafuranose or 1,6-dideoxy-azapyranose is disclosed. In such a process, an azido-substituted α-ketose phosphate having a five- or a six-carbon chain is hydrogenated in the presence of a palladium catalyst. The carbon atom bearing the azido substituent and the carbon atom of the keto group of the α-ketose phosphate starting material are separated by two or three carbon atoms.

16 Claims, No Drawings

OTHER PUBLICATIONS

Bernotas et al., *Tetrahedron Lett.* 1985, 26, 1123.
von der Osten et al., *J. Am. Chem. Soc.* 1989, 111, 3924.
Pederson et al., *Heterocycles* 1989, 28, 477.
Straub et al., *J. Org. Chem.* 1990, 55, 3926.
Durrwachter et al., *J. Am. Chem. Soc.* 1986, 108, 7812.
Durrwachter et al. *J. Org. Chem.* 1988, 53, 4175.
Bednarski et al. *Tetrahedron Lett.* 1986, 27, 5807.
Hamana et al., *J. Org. Chem.* 1987, 52, 5492.
Pederson et al., *J. Org. Chem.*, 55, 4897 (1990).
Ozaki et al., *J. Am. Chem Soc.* 1990, 112, 4970.
Nelson et al., *J. Med. Chem.*, 19:153 (1976).
Weinreb et al., *Tetrahedron Lett.* 1986, 2099.
Lalegerie et al., *Biochemie* 1982, 64, 977.
Withers et al., *J. Am. Chem. Soc.* 1988, 1100, 8551.
Withers et al., *J. Am. Chem. Soc.* 1990, 112, 5887.
Schweden et al., *Arch. Biochem. Biophys.*, 1986, 248,335.
Dale et al., *Biochemistry,* 1985, 24, 3530.
Reitz, et al., *Tetrahedron Lett,* 31 (47):6777–6750 (1990).
Valentin-Hansen et al., *EMBO J.,* 1:317 (1982).
Lipshutz et al., *J. Am. Chem. Soc.,* 104:2305 (1982).
Pederson et al., *Tetrahedron Lett.,* 47:2643 (1991).
Wong et al., *Tet. Letters,* 32(37);4867–4870 (1991).
Paulsen et al., *Liebigs Ann. Chem.,* pp. 953–957 (1990).
Kajimoto et al., *J. Am. Chem. Soc.,* 113:6187–6196 (1991).
Liu et al., *J. Org. Chem.,* 56(22):6280–6289 (1991).
Kajimoto et al., *J. Am. Chem. Soc.,* 113:6678–6680 (1991).

PROCESS FOR FORMING OMEGA-DEUXY-AZASUGARS

STATEMENT OF GOVERNMENT SUPPORT

This invention was made with government support under Grant #GM 44154 awarded by The National Institutes of Health. The government has certain rights in the invention.

CROSS REFERENCE TO RELATED APPLICATIONS

This application is a continuation-in-part of copending application Ser. No. 07/707,600 filed May 30, 1991, now abandoned.

TECHNICAL FIELD

The present invention relates to azasugar compounds, and more particularly to omega-deoxy-azapyranose and azafuranose compounds, their manufacture and use.

BACKGROUND ART

Carbohydrates are a large class of natural substances that structurally are polyhydroxycarbonyl compounds and their derivatives. Carbohydrates generally correspond to the formula $(C)_n(H_2O)_n$, where n is an integer usually greater than 3.

Monosaccharides are simple carbohydrates that cannot be further hydrolyzed into simpler types of carbohydrate. A monosaccharide having a six-membered ring is referred to as a pyranose, whereas a five-membered ring monosaccharide is referred to as furanose. A pyranose or furanose lacking one or more hydroxyl groups normally present in a carbohydrate is referred to as a deoxy-pyranose or deoxy-furanose, with the carbon chain position at which the hydroxy is absent being indicated.

Azasugars are a class of saccharides in which the ring oxygen is replaced by an imino group (—NH—). A six-membered ring azasugar can be referred to as an azapyranose or a polyhydroxylated piperidine compound. A five-membered ring azasugar can be referred to as an azafuranose or a polyhydroxylated pyrrolidine. An azasugar can also be named as an aza derivative of an otherwise systematically or trivially named pyranose or furanose monosaccharide.

One group of azasugars described herein are derived from piperidines (azapyranoses), can be hyrdroxylated at the 3-, 4- and 5-positions, have hydrogen at the 6-position and can have a methyl group or hydrogen at the 2-position, the 1-position being the nitrogen atom, in piperidine nomenclature. Dideoxyazapyranoses are the polyhydroxylated piperidines as discussed above, that have either a methyl group or hydrogen at the 5-position, hydrogen at the 1-position and can have hydroxyl groups elsewhere on the ring, as above, in pyranose nomenclature. Pyranose nomenclature and numbering will usually be used herein for six-membered ring compounds, unless otherwise specified.

Another group of azasugars described herein are derived from pyrrolidines (azafuranoses). These compounds can be hydroxylated at the 3 and 4 positions, have a hydroxymethyl group at the 5-position, and a methyl or hydroxymethyl at the 2-position, the 1-position being the nitrogen atom, in pyrrolidine nomenclature. A 2-hydroxymethyl group in pyrrolidine nomenclature corresponds to a 1-hydroxymethyl or 4-hydroxyl group in furanose nomenclature. Dideoxyazafuranoses are the polyhydroxypyrrolidines discussed above that have a methyl or hydroxymethyl at the 4-position, hydrogen or hydroxymethyl at the 1-position, and can have hydroxyl groups at the other positions, using furanose numbering. Pyrrolidine nomenclature and numbering will usually be used herein for these azasugars, unless otherwise specified.

Azasugars and their derivatives have been identified as potent glycosidase inhibitors [Paulsen et al., *Adv. Carbohydr. Chem.* 1968, 21, 115; Fellows, *Chem. Br.* 1987, 22, 842; Truscheit et al., *Angew. Chem. Int. Ed. Engl.* 1981, 22, 744; Inouye et al., *Tetrahedron* 1968, 24, 2125; Muller, in *Biotechnology*, Rehm, H.-J. et al., eds., VCH Verlagsgesellschaft Weinheim 1985, Vol. 4, Chapter 18]. As such, azasugars can be useful for treating metabolic disorders such as diabetes [Liu, *J. Org. Chem.* 1987, 52, 4717; Bayer et al., Ger. Offen. DE 3620645; Anzeveno et al., *J. Org. Chem.* 1989, 111, 2539; Yoshikuni et al., *J. Pharmacobio-Dyn* 1988, 111, 356] or as antiviral agents [Karpas et al., *Proc. Natl. Acad. Sci.* 1988, 85, 9229; Walker et al., *Proc. Natl. Acad. Sci.* 1987, 84, 8120; Winkler et al., *J. Med. Chem.* 1989, 32, 2084], as antimicrobial [Evans et al. *J. Phytochemistry* 1985, 24, 1953] and as anticancer agents [Humphries, M. J., et al. *Cancer Res.* 1986, 46, 5215].

Despite their clear usefulness, there is still a need for an effective synthesis of novel azasugars and their derivatives [Fleet, *Chem. Br.* 1989, 25, 287 and references cited therein; Bernotas et al., *Tetrahedron Lett.* 1985, 26, 1123; Setoi et al. *Chem. Pharm. Bull,* 1986, 34, 2642; Legler et al., *Carbohydr. Res.* 1984, 128, 61; Kinast et al., *Angew. Chem. Int. Ed. Enal.* 1981, 20, 805; Hanesian, *Chem. Ind.* 1966, 2126; Schmidt et al., *Justus Liebigs Ann. Chem.* 1989, 5, 423; Pederson et al., *Tetrahedron Lett.* 1988, 29, 4645; Ziegler et al., *Angew. Chem. Int. Ed. Engl.* 1988, 29, 716; Buchanan et al., *J. Chem. Soc. Perkin Trans,* 1990, 699; Fleet et al., *J. Chem. Soc. Perkin Trans.* 1989, 665; Dondoni et al., *J. Chem. Soc. Chem. Commun.* 1990, 854; Fleet et al., *Chem. Lett.* 1986, 1051; Chen et al., *Tetrahedron Lett.* 1990, 31, 2229; Ciufolini et al., *J. Am. Chem. Soc.* 1989, 111, 3473].

Naturally occurring azasugars include 1-deoxynojirimycin (1,5-dideoxy-1,5-imino-D-glucitol), 1-deoxymannojirimycin (1,5-dideoxy-1,5-imino-D-mannitol), and castanospermine (1,6,7,8-tetrahydroxyoctahydroindolizine). 1-Deoxynojirimycin was isolated from plants of the genus Morus [Yagi et al., *Nippon Nogei Kagaku Kaishi* 1976, 50, 5751; Vasella et al., *Helv. Chim. Acta,* 1982, 65, 1134] and from strains of Bacillus [Daigo et al., *Chem. Pharm. Bull.* 1986, 34, 2243]. 1-Deoxymannojirimycin was isolated from the legume Lonchocarpus [Fellows et al., *J. C. S. Chem. Comm.* 1979, 977]. Castanospermine is a plant alkaloid isolated from seeds of an Australian chestnut tree, *Castanospermum australe* [Saul et al. *Arch. Biochem. Biophys.* 1983, 221, 593]. Isolation of azasugars from nature is often expensive and time consuming. Therefore, several methods have been developed for the synthesis of these important compounds.

Both synthetic and semi-synthetic routes have been used in these syntheses [Inouye et al., *Tetrahedron* 1968, 24, 2125; Paulsen et al., *Chem. Ber,* 1967, 100, 802; Saeki et al., *Chem. Pharm. Bull.* 1968, 16, 2477; Paulsen et al., *Adv. Carbohydr. Chem.* 1968, 23, 115; Kinast et al., *Angew. Chem. Int. Ed. Engl.* 1981, 20, 805; Bernotas et al., *Tetrahedron Lett.* 1984, 25, 165; Bernotas, *Tetrahedron Lett,* 1985, 26, 1123; Setoi et al., *Chem. Pharm. Bull.*

1986, 34, 2642; Iida, *J. Org. Chem.* 1987, 52, 3337). Natural sugars have been used as starting materials, but multiple protection and deprotection steps are required. For example, glucose was used in the synthesis of 1-deoxynojirimycin and 1-deoxymannojirimycin [Fleet, *Chem. Br.* 1989, 25, 287 and references cited therein; Bernotas et al., *Tetrahedron Lett,* 1985, 26, 1123; Chen et al., *Tetrahedron Lett,* 1990, 31, 2229).

An enzymatic synthesis based on fructose-1,6-diphosphate (FDP) aldolase (EC 4.1.2.3) has been recently developed and has proven to be a powerful approach for the synthesis of some azasugars [Pederson et al., *Tetrahedron Lett.* 1988, 29, 4645; von der Osten et al., *J. Am. Chem. Soc.* 1989, 111, 3924; Pederson et al., *Heterocycles* 1989, 28, 477; Ziegler et al., *Angew, Chem. Int. Ed. Engl.* 1988, 29, 716; Straub et al., *J. Org. Chem.* 1990, 55, 3926]. This enzymatic method involves the use of FDP aldolase from either rabbit muscle or *Escherichia coli* to catalyze the aldol condensation of dihydroxyacetone phosphate (DHAP; a donor substrate) with any of a number of possible omega-azidoaldehydes as a second, acceptor substrate [Durrwachter et al., *J. Am. Chem. Soc.* 1986, 108, 7812; Durrwachter et al. *J. Org. Chem.* 1988, 53, 4175; Pederson et al., *Tetrahedron Lett.* 1988, 29, 4645; Bednarski et al. *Tetrahedron Lett,* 1986, 27, 5807]. The omega-azidoketose phosphate produced is dephosphorylated and then reductively cyclized to form a deoxynojirimycin compound.

For instance, if DHAP is reacted with (RS)-3-azido-2-hydroxypropanal in the presence of FDP aldolase, the 2-epimers, 1-deoxynojirimycin and 1-deoxymannojirimycin, are produced upon catalytic reductive amination of the dephosphorylated enzyme reaction products [Pederson, R. L., et al. *Tetrahedron Lett.* 1988, 29; 4645].

After synthesis, 1-deoxynojirimycin can then be easily converted into castanospermine [Hamana et al., *J. Org. Chem.* 1987, 52, 5494]. The latter compound has been shown to inhibit the processing of the AIDS virus gp160 envelope protein precursor, and to modify the envelope glycoprotein, thus affecting the ability of the virus to enter cells [Walker et al., *Proc. Natl. Acad. Sci.* 1987, 84, 8120].

The synthesis of hydroxylated piperidines and pyrrolidines from dicarbonyl sugars via a one-step double reductive amination reaction has recently been reported. Reitz, et al., *Tetrahedron Lett,* 31 (47):6777–6750 (1990). According to such a synthetic scheme, 2,5-anhydro-imino-D-glucitol and 1-deoxynojirimycin were prepared by reacting 5-keto-D-fructose and 5-keto-D-glucose, respectively, with benzhydrylamine (NaCNBH$_3$, MEOH).

Each of the above azapyranoses and azafuranoses thus far prepared has had two hydrogens at the 1-position of the azapyranose (or azafuranose) ring and a hydroxyl group at the 6- or 5-position (omega-position) carbon atom of the pyranose or furanose chain; i.e., the last carbon in the chain or the omega-position. Further, naturally occurring pyranose and furanose sugars found in man and other mammals contain a 6- or 5-position hydroxyl group, respectively.

On the other hand, many pyranose sugars in many microbes such as bacteria, insects and plants are free of a 6- or omega-position hydroxyl group. Such 6-or omega-dehydroxy (-deoxy) sugars are rare, if present at all, in man and other mammals.

It would therefore be beneficial if a 6- or omega-deoxy azapyranose could be prepared that bears a structural similarity to the omega-deoxy-pyranoses that are present in microbes. The disclosure that follows describes the synthesis and activity of several omega-deoxy-azapyranose compounds as well as the synthesis of omega-deoxy azafuranose.

BRIEF SUMMARY OF THE INVENTION

The present invention contemplates omega-deoxy azapyranose compounds, their use, processes of manufacture of omega-deoxy-azapyranose and omega-deoxy-azafuranose compounds, and intermediate compounds.

More particularly, an omega-deoxy-azapyranose is contemplated. That compound has the formula I:

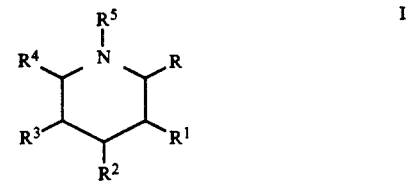

wherein R is hydrogen, hydroxymethyl, $C_1$–$C_6$ alkyl, —CHOHCH$_2$OH or carboxylic acid;

$R^1$ is hydrogen, hydroxyl, $C_1$–$C_4$ alkoxy, halide, or $NR^6R^7$ where $R^6$ is hydrogen or $C_1$–$C_4$ alkyl and $R^7$ is hydrogen, $C_1$–$C_4$ alkyl, $C_1$–$C_4$ acyl or $NR^6R^7$ together form a cyclic imido group that contains 4–8 carbon atoms;

$R^2$ is hydrogen or hydroxyl;

$R^3$ is hydrogen, hydroxyl or methyl;

$R^4$ is hydrogen or methyl; with the provisos (i) that only one of $R^3$ or $R^4$ is methyl, and (ii) where one of R or $R^4$ is methyl, the other of R or $R^4$ is hydrogen and $R^1$, $R^2$ and $R^3$ are hydroxyl, the stereoconfiguration of R and $R^{1-4}$ is other than that of glucose, mannose or fucose;

$R^5$ is selected from the group consisting of hydrogen, $C_1$–$C_{12}$ alkyl, $C_7$–$C_{10}$ aralkyl and $C_1$–$C_{12}$ acyl, or $>N$-$R^5$ is a $C_1$–$C_{12}$ alkyl or $C_7$–$C_{10}$ aralkyl N-oxide; and the deoxy-azapyranose contains at least two hydroxyl groups.

In some preferred compounds, R is hydrogen or hydroxymethyl and, preferably, hydrogen. Where R is hydrogen, $R^2$ and $R^3$ are each preferably hydroxyl. In other preferred compounds, $R^4$ is methyl.

Another aspect of this invention contemplates a general process of forming a 5- or 6-deoxy-azasugar; i.e., an omega-deoxy-azasugar. In accordance with that method, an azido-substituted α-ketose compound having a five- or six-carbon chain is hydrogenated in the presence of a palladium catalyst. Preferably, the azido-substituted α-ketose phosphate compound. The carbon atom of the azido substituent and the carbon of the keto group are separated in the chain by two or three carbon atoms, respectively. The 6-deoxy-azapyranose or 5-deoxy-azafuranose thus prepared is preferably recovered.

Also contemplated by the present invention is a composition that comprises a glycosidase inhibiting amount of a before-described omega-deoxy-azapyranose compound dispersed in an aqueous medium. The aqueous medium is preferably pharmaceutically acceptable.

DETAILED DESCRIPTION OF THE INVENTION THE COMPOUNDS

A compound of the invention is an omega-deoxy-azapyranose. The use of "azapyranose" in the name implies that a compound of the invention contains a 6-membered ring having a nitrogen atom in the ring in place of the oxygen of a pyranose. The nitrogen atom is an imino nitrogen (—NH—) in the parent azasugar and in many preferred compounds but the remaining valances of the nitrogen can be used as is discussed hereinafter.

Use of the word stem "pyranose" also indicates that a compound of the invention, unless otherwise specified, is a carbohydrate, and therefore corresponds to the chemical formula $(C)_n(H_2O)_n$, as discussed before. As a consequence, a contemplated azapyranose has a plurality of hydroxyl groups, or is a polyhydroxy piperidine compound, unless otherwise indicated. A contemplated azapyranose contains at least two hydroxyl groups.

A compound of the invention is also an omega-deoxy compound. By that it is meant that the last or "omega" carbon atom of the chain that makes up the azapyranose backbone lacks a hydroxyl group. Particularly preferred compounds contain a chain of six carbon atoms, so that particularly preferred compounds are 6-deoxy-azapyranose compounds.

A compound of the invention has structural formula I:

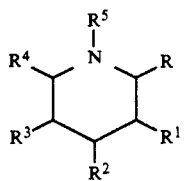

wherein R is hydrogen, hydroxymethyl (—CH$_2$OH), $C_1$-$C_6$ alkyl, dihydroxyethyl (—CHOHCH$_2$OH) or carboxylic acid (—CO$_2$H);

$R^1$ is hydrogen, hydroxyl, $C_1$-$C_4$ alkoxy, halide, or NR$^6$R$^7$ where R$^6$ is hydrogen or $C_1$-$C_4$ alkyl and R$^7$ is hydrogen, $C_1$-$C_4$ alkyl, $C_1$-$C_4$ acyl or NR$^6$R$^7$ together form a cyclic imido group that contains 4–8 carbon atoms;

$R^2$ is hydrogen or hydroxyl;

$R^3$ is hydrogen, hydroxyl or methyl;

$R^4$ is hydrogen or methyl; with the provisos (i) that only one of $R^3$ or $R^4$ is methyl; and (ii) where one of R or $R^4$ is methyl, the other of R or $R^4$ is hydrogen and $R^1$, $R^2$ and $R^3$ are hydroxyl, the stereoconfiguration of R and $R^{1-4}$ is other than that of glucose, mannose or fucose;

$R^5$ is selected from the group consisting of hydrogen, $C_1$-$C_{12}$ alkyl, $C_7$-$C_{10}$ aralkyl and $C_1$-$C_{12}$ acyl, or >N-$R^5$ is a $C_1$-$C_{12}$ alkyl or $C_7$-$C_{10}$ aralkyl N-oxide; and;

the deoxy-azapyranose contains at least two hydroxyl groups.

In the above formula I, and in the other formulas utilized herein, only one group at each of the ring carbon atoms is shown. The fourth, unshown, group bonded to each of those ring carbons is a hydrogen atom, as would be present in an unsubstituted carbohydrate.

An azido ketose used in a process of the invention would normally contain a hydroxyl group on each carbon atom of the chain except for the carbon of the keto group. The azido group replaces one hydroxyl group and an azido ketose is properly named as a deoxy-azido ketose. Similarly, an azapyranose where any of R and $R^{1-4}$ is other than hydroxyl should also be named as a deoxy compound. Such proper names are long and cumbersome to use. As a consequence, only the omega- and 1,omega-deoxy name will be used in most places, with other substituents being named without the use of "deoxy".

The above structural formula also does not show the orientation of groups R and $R^{1-4}$ relative to the plane of the ring. Each of the α- and β-orientations is contemplated for each of R and $R^{1-4}$, so those substituent groups are shown generally. The straight lines between the ring and the substituent groups are meant to imply that substituents can be in the α- or β-configuration. Darkened wedge-shaped lines indicate that a substituent is in a β-configuration, extending upwardly from the plane of the ring, whereas dashed wedge-shaped lines indicate a substituent in the α-configuration, extending downwardly from the plane of the ring.

The orientation of a substituent is a function of the precursor molecule, and the substituent orientation can be varied as desired. As will be discussed hereinafter, particular orientations of R and $R^{1-4}$ are preferred.

Turning more specifically to the substituent groups, R and $R^{1-4}$, it is first to be noted that a $C_1$-$C_4$ alkyl group is also present in a $C_1$-$C_4$ alkoxy group, so only the alkyl groups will be discussed. Contemplated $C_1$-$C_4$ alkyl groups include methyl, ethyl, propyl, isopropyl, n-butyl, sec-butyl, iso-butyl and t-butyl. $C_1$-$C_4$ acyl groups are the corresponding acyl groups to $C_1$-$C_4$ alkyl groups, with the understanding that sec- and t-butyl have no corresponding acyl groups.

Preferred $C_1$-$C_4$ alkyl and alkoxy groups are methyl, ethyl and methoxy and ethoxy, respectively. A preferred $C_1$-$C_4$ acyl group is acetyl. As initially synthesized using the process discussed hereinafter, $R^5$ is hydrogen. Hydrogen is thus a preferred $R^5$ group. These preferences relate to all of the compounds herein.

An NR$^6$R$^7$ group is seen to be a free amine (—NH$_2$—) a mono- or di-alkyl substituted amine, an acyl amine, an acyl alkyl amine where the alkyl and acyl groups are as described before, or a cyclic imido group that contains 4–8 carbon atoms. Exemplary cyclic imido groups include succinimido, methylsuccinimido, maleimido and phthalimido groups.

For $R^5$, an alkyl or acyl group can be longer than those discussed previously. Thus, the same $C_1$-$C_4$ alkyl or acyl groups can be utilized, as can longer groups such as hexyl, octyl, nonyl, decyl, undecyl, dodecyl and their corresponding acyl groups, as well as benzyl and benzoyl groups. The presence of a $C_1$-$C_{12}$ acyl or alkyl group improves lipid solubility for the dideoxy-azapyranose. A contemplated $C_7$-$C_{10}$ aralkyl group includes benzyl, phenethyl, (p-ethyl)phenethyl, and the like.

An >N-$R^5$ can also be a $C_1$-$C_{12}$ alkyl or a $C_7$-$C_{10}$ aralkyl N-oxide. Here, the alkyl group is as discussed above, and the alkylated tertiary nitrogen atom is oxidized to form the N-oxide. The symbol ">" is used to show the remaining valences of the nitrogen that are bonded to ring carbon atoms.

Turning to specific compounds, it is preferred that R is hydroxymethyl; $R^1$, $R^2$ and $R^3$ are all hydroxyl; R4 is hydrogen; $R^5$ is hydrogen; and the stereoconfiguration of R and $R^{1-4}$ is that of talose. That preferred compound is designated herein as Compound 124 and is named D-1-deoxytalonojirimycin.

Turning to particular embodiments, it is preferred that R is hydrogen or hydroxymethyl and, more preferred that R is hydrogen. According to such a preferred embodiment, the compounds of the present invention conform to structural formula II, below.

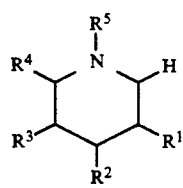

where $R^1$–$R^5$ are as defined for formula I, with the proviso that where $R^4$ is methyl and $R^1$, $R^2$ and $R^3$ are all hydroxyl, the stereoconfiguration of $R^{1-4}$ is other than that of fucose.

Turning to particular compounds, it is preferred, in formula II, that each of $R^2$ and $R^3$ is hydroxyl. Within that preference, $R^1$ can preferably also be hydroxyl, halide such as fluoride, or N-acyl such as N-acetyl.

A particularly preferred group of compounds of structural formula II, have a six-carbon backbone chain and are 1,6-dideoxy-azapyranose compounds. Those compounds conform to structural formula III, below.

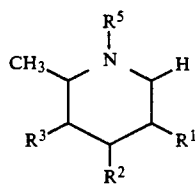

wherein $R^2$ and $R^5$ are as before-defined, $R^1$ is as before, but excluding hydrogen and $C_1$–$C_4$ alkyl, and $R^3$ is hydrogen or hydroxyl, with the proviso that where $R^1$, $R^2$ and $R^3$ are hydroxyl, the stereoconfiguration of $CH_3$ and $R^{1-3}$ is other than that of fucose.

$R^2$ and $R^3$ for these compounds are each preferably hydroxyl as is shown in structural formula IV, below, where $R^1$ and $R^5$ are as immediately above.

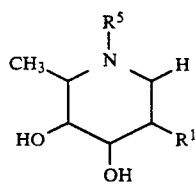

One group of such preferred compounds have the specific structural formulas shown below of Compounds 3a–f.

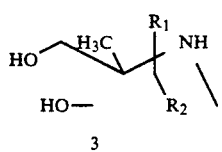

3 a: $R_1$ = OH, $R_2$ = H
b: $R_1$ = AcNH, $R_2$ = H
c: $R_1$ = H, $R_2$ = OH
d: $R_1$ = H, $R_2$ = AcNH
e: $R_1$ = F, $R_2$ = H
f: $R_1$ = OEt, $R_2$ = H

The above compounds can also be depicted by the formula below where $R_1$ is hydroxyl, N-acetyl, fluoride or ethoxy.

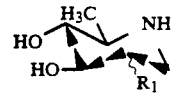

A subgroup of compounds of Formula III in which $R^2$ and $R^3$ are each hydroxyl are the compounds in which $R^1$, $R^2$ and $R^3$ are each hydroxyl. Exemplary specific structural formulas for four of these compounds in addition to those above are shown below.

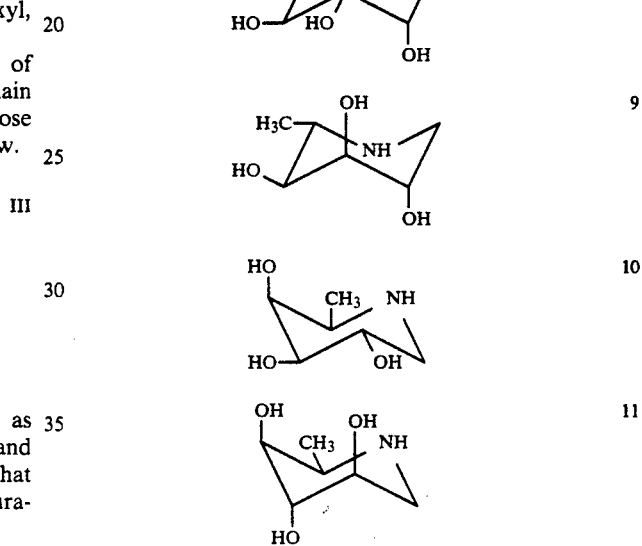

Another group of preferred compounds conform to structural formula V, shown below. Formula V is similar to formula II, but the R groups are more limited than those of structural formula II.

wherein $R^1$ is hydrogen or $C_1$–$C_4$ alkyl;
$R^3$ is hydrogen or hydroxyl;
$R^4$ is hydrogen or methyl; and
$R^5$ is as described before.

Exemplary Compounds 14a–c of structural formula V are illustrated below. $R^5$ is formula V is also preferably hydrogen.

-continued

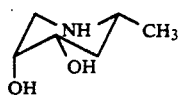
14b

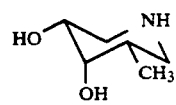
14c

Compound Preparation

Another aspect of the present invention relates to the synthesis of some of the above omega-deoxy azapyranoses as well as the synthesis of 1,6-dideoxy-azapyranoses and 1,5-dideoxy-azafuranoses; i.e., 1,omega-dideoxy-azasurgars. In accordance with this process aspect, an azido-substituted α-ketose phosphate compound having a five- or six-carbon chain is reductively cyclized by hydrogenation in the presence of a palladium catalyst. The carbon atom of the azido substituent and the carbon atom of the keto group are separated in the chain by two or three carbon atoms, respectively, or counting differently, the keto group is separated from the azido substituent by 3 or 4 carbon atoms.

An azido-substituted α-ketose phosphate used to form an omega-deoxy-azapyranose can be prepared in a number of standard organic chemical manners, as is apparent from their relatively simple structures. Such standard preparations tend, however, to provide the desired azido α-ketose phosphate compounds in relatively low yields of mixtures. Those mixtures can be separated prior to reductive cyclization-hydrogenolysis by usually used chromatographic techniques.

It is preferred however, to utilize enzymatic syntheses to form the desired azido α-ketose phosphate starting materials. Enzymes that are particularly useful for such syntheses are the aldolases. According to such an enzymatic synthetic method, a phosphorylated donor ketone (e.g. dihydroxyacetone phosphate, DHAP) is mixed with an azido-aldehyde (e.g. 2-azido-3-hydroxy-propanal) in the presence of a catalytic amount of an aldolase enzyme to form a reaction mixture. The reaction mixture is then maintained under biological reaction conditions for a period of time sufficient to form the desired azido-substituted α-ketose phosphate compound.

Biological reaction conditions are those that maintain the activity of the aldolase as well as the structural integrity of the formed azido-substituted α-ketose phosphate compound. Those conditions include a temperature range of about 0° C. to about 45° C., a pH value range of about 5 to about 9 and an ionic strength varying from that of distilled water to that of about one molar sodium chloride. Methods for optimizing such conditions are well known in the art.

The synthesis of omega-deoxy azapyranoses according to such a synthetic process is shown below in Scheme 1, where R is as defined above for formula I.

Scheme 1

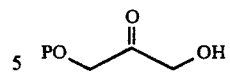

+ aldolase →

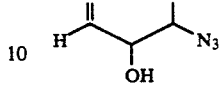

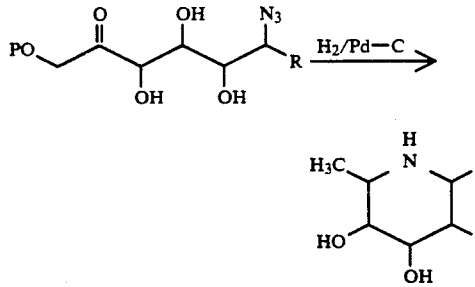

The reductive cyclization that is used in each of the generalized reactions shown in Scheme 1 can provide two stereoisomeric products, depending upon the side of the cyclic imine intermediate to which the hydrogen is added. Schemes 4–7, hereinafter, illustrate each of the possible products from those reductive cyclizations.

In actual practice, it is found that a mixture of both possible cyclization products is obtained when hydrogenation is carried out without prior dephosphorylation. The isomer in which the methyl and adjacent ring hydroxyl groups are trans predominates in the mixture.

On the other hand, where the azido-substituted α-ketose phosphate compound is first dephosphorylated and then reductively cyclized, substantially only one of the two possible hydroxymethyl compounds is obtained. That obtained hydroxymethyl compound has a configuration in which the hydroxymethyl group, which formerly bore the phosphate, is trans to the adjacent hydroxyl group.

A. Reductive Cyclization by Hydrogenation

In carrying out the hydrogenation of the process of Scheme 1, substantially any standard palladium catalyst can be used. Exemplary catalysts include palladium powder, palladium on activated carbon (Pd/C), palladium on alumina, palladium on barium sulfate and palladium on calcium carbonate. Palladium on activated carbon (charcoal) is a preferred catalyst.

The hydrogenation is carried out at greater than atmospheric pressure such as at about 40–60 pounds per square inch (psi). A usual hydrogenation solvent such as water, ethanol or methanol, or mixtures thereof is also used.

A hydrogenation useful herein is thus seemingly similar to that used in the art to convert azido α-ketols to various nojirimycin derivatives. An important distinction exists however between those reactions and the hydrogenations described herein.

That distinction lies in the presence of a terminal (omega) phosphate group adjacent to (α to) the keto group of a compound used herein that is lost during the reductive cyclization and is replaced by a hydrogen atom. Thus, a compound that is reductively cyclized herein is an azido α-ketose phosphate. In the reductive cyclizations of the art, an omega-hydroxyl group was present in the starting azido ketol adjacent to the keto group, and that hydroxyl was retained in the cyclized azasugar.

Several known omega-hydroxyl azasugars have been prepared using an azido α-ketose phosphate as an intermediate. However, that intermediate was always dephosphorylated prior to the reductive cyclization step so that it was previously unknown that an omega-deoxy-azapyranose could be directly prepared during a palladium-catalyzed reductive cyclization.

No precedent is known for this dephosphorylating hydrogenolysis reaction. Treatment of glucose 6-phosphate or dihydroxyacetone phosphate under the same conditions showed no reaction, thereby implicating the ring nitrogen atom in the hydrogenolysis reaction. Preliminary studies indicate that an imine phosphate derivative may be an intermediate in the loss of the phosphate group.

B. Aldolase Catalyzed Formation of Azido-substituted α-ketose Phosphate

The aldolase-catalyzed reaction of Scheme 1 is an aldol condensation. According to such a condensation reaction, a phosphorylated donor ketone (e.g. dihydroxyacetone phosphate) is reacted with an azido-aldehyde in the presence of an aldolase enzyme. Of particular relevance to the present invention are fructose-1,6-diphosphate (FDP) aldolase (EC 4.1.2.3), rhamnulose-1-phosphate (Rham-1-P) aldolase (EC 4.1.2.19), fuculose-1-phosphate (Fuc-1-P) aldolase (EC 4.1.2.17), tagatose-1,6-diphosphate (TDP) aldolase and 2-deoxyribose-5-phosphate aldolase (DERA, EC 4.1.2.4).

Each of those enzymes can utilize dihydroxyacetone phosphate (DHAP) as a donor substrate and a number of aldehydes as acceptor substrates to form azido-substituted α-ketose phosphate compounds having new stereogenic centers with, for example, D-threo (3S,4R), L-threo (3R,4S), L-erythro (3R,4R), D-erythro (3S,4S), D-ribo (2R), D-glycero-D-allo (2R,3S) configurations.

By selection of the aldolase enzyme and the configuration of an azido aldehyde, one can control the isomeric configuration of the azido-substituted α-ketose phosphate compound and, thus, the stereochemistry of the cyclized azasugar. If formation of an azasugar with a desired configuration about a particular bond is not favored by the enzymatic aldol condensation leading to the azido α-ketose phosphate, that stereochemistry can be changed in the azido α-ketose phosphate or azasugar by selective blocking of hydroxyl or other reactive groups and inversion of the configuration of the desired substituent using well known organic chemical techniques.

Exemplary syntheses of precursor azido aldehydes, azido α-ketose phosphate and azasugars are discussed hereinafter.

It is to be pointed out that an azido-substituted α-ketose phosphate can exist in solution in a straight chain or cyclic, hemiacetal form. Upon reductive cleavage of the azido group in forming a primary amine that becomes the nitrogen atom of the azapyranose, the hemiacetal rearranges to form a cyclic imine that is further reduced to the azasugar.

Inasmuch as a primary amine substituent present in an azido α-ketose phosphate used to form an azapyranose could also form a cyclic imine that would form an undesired azasugar on further reduction, a primary amine present as an $R^1$ group of an azapyranose is blocked during the hydrogenation step as with a t-Boc, Cbz or similar group that is removed after the reductive cyclization-hydrogenolysis step. An $N$-$C_1$-$C_4$ acyl group needs no added blocking group for the amine.

Aside from a primary amino group, the substituent groups R and $R^{1-4}$ present in a final omega deoxy-azapyranose can be present during the reduction step of the synthesis and need no blocking groups. If desired, however, blocking groups insensitive to the hydrogenation reaction can be utilized and then removed or the substituent groups replaced, as desired. The freedom from the need for blocking groups is, however, one of the advantages of this synthetic method.

It is to be understood that each of the above aldolase enzymes can also be used to form 1,5-dideoxy-azafuranose (pyrrolidine) compounds using DHAP as the donor enzyme substrate as shown below in Scheme 2, where R is defined above in formula I.

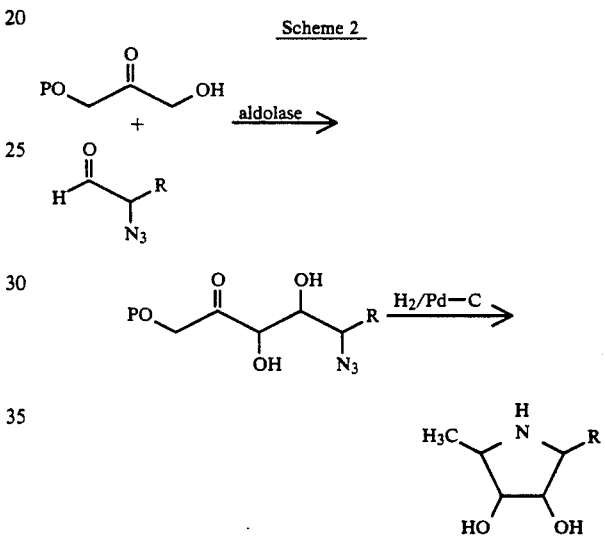

Scheme 2

An exemplary acceptor substrate for formation of an azafuranose is 2-azido-3-hydroxypropanal. The azasugar products prepared from each enzyme are diastereomers. An exemplary synthesis of one 1,5-dideoxy-azafuranose using FDP aldolase is described hereinafter. A variety of isomeric azafuranoses can be made from DHAP and 2-azido-3-hydroxypropanal by using other aldolase enzymes (See Scheme 11, hereinafter).

C. Stereochemistry of Formed Azasugars

The stereochemistry of formed azasugars is controlled by the isomeric configuration of aldehyde substrates and the use of particular aldolase enzymes.

3-Azido-2-hydroxypropanal can exist in four isomeric states: 3(R)-azido-2(R)-hydroxypropanal; 3(R)-azido-2(S)-hydroxypropanal; 3(S)-azido-2(S)-hydroxypropanal; and 3(S)-azido-2(R)-hydroxypropanal. Those isomers are prepared by the acid hydrolysis of particular isomers of four-carbon epoxy compounds as shown below in Scheme 3, whose reagents and reactions are discussed hereinafter.

Scheme 3

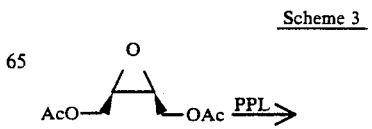

-continued
Scheme 3

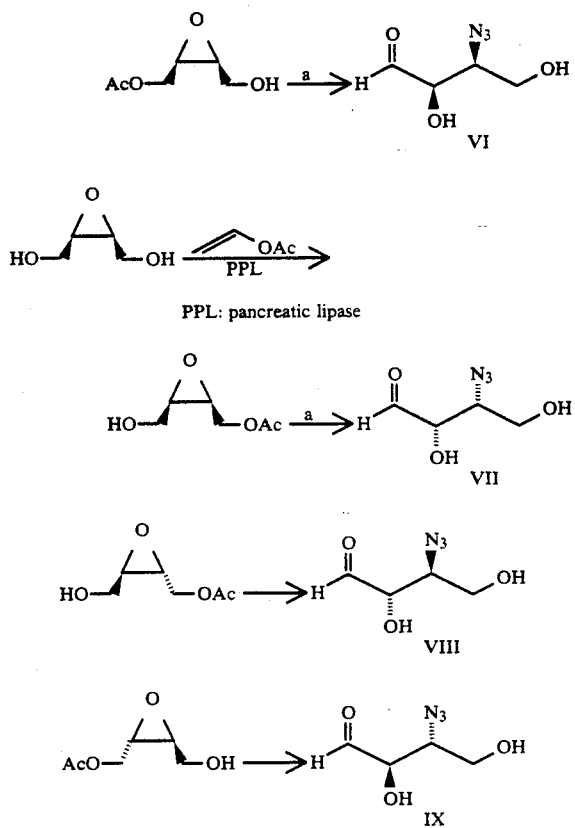

a: 1) PCC
   2) EtOH/H+
   3) NaN₃
   4) H+

The acid hydrolysis of the epoxy compounds (step a of Scheme 3) is carried out by reacting such compounds with pyridinium chlorochromate (PCC), acidic ethanol (EtOH/H+), sodium azide (NaN₃) and acid (H+). Cis-2,3-epoxy-1-acetoxy-4-butanol and cis-2,3-epoxy-4-acetoxy-1-butanol are prepared from cis-2,3-epoxy-1,4-diacetoxybutane and cis-2,3-epoxy-1,4-butanediol, respectively, in a reaction catalyzed by pancreatic lipase (PPL). Trans-2,3-epoxy-4-acetoxy-1-butanol and trans-2,3-epoxy-1-acetoxy-4-butanol are reported by Grandjean et al., *Tetrahedron Lett.*, 23:3043 (1991).

1. Fructose-1,6-diphosphate (FDP) Aldolase

As shown below in Scheme 4, Compounds VI, VII, VIII and IX from Scheme 3 are condensed with DHAP in the presence of FDP aldolase (step a) to form azidoketose-phosphate Compounds X, XI, XII and XIII, respectively. Compounds X, XI, XII and XIII are then reductively cyclized by hydrogenation (step b) to yield azasugar Compounds 100, 101, 102 and 103, respectively. Compounds 100, 101; 102 and 103 differ from each other only in the orientation of the hydroxymethyl at the C-1 position and the hydroxyl at the C-2 position. It can thus be seen that the isomeric form of the 3-azido-2-hydroxylpropanal dictates the orientation of the C-1 and C-2 substituent groups in the resulting azasugars.

FDP-Aldolase can be obtained from commercial sources (Sigma Chemical Co., St. Louis, Mo.) or isolated from animal tissues such as rabbit muscle (See Example 1 hereinafter).

Scheme 4

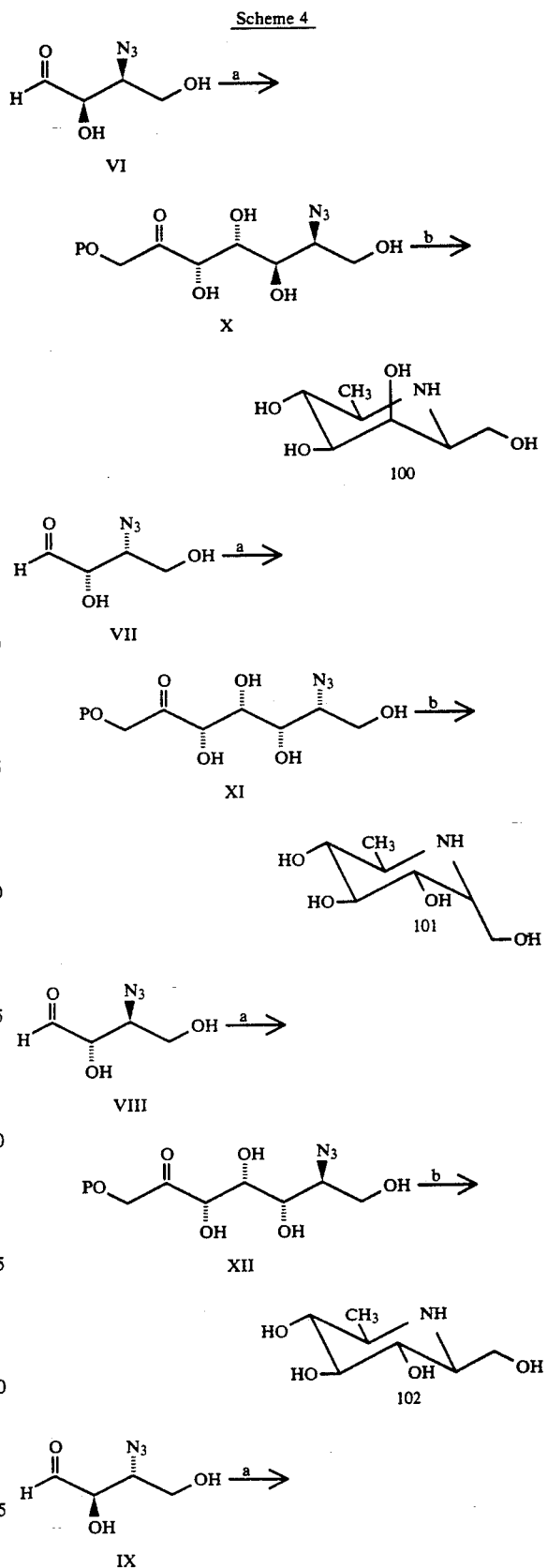

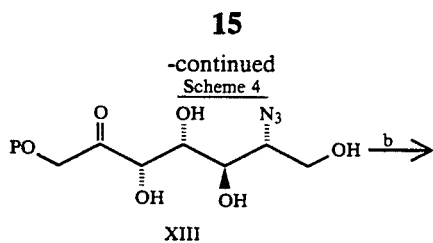
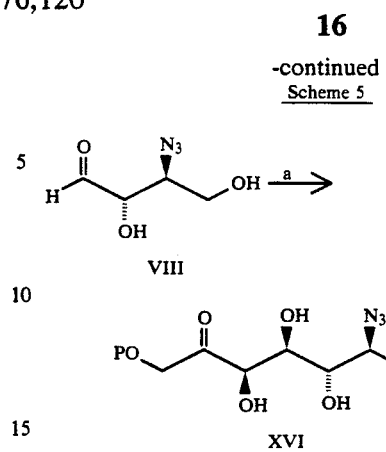

2. Rhamnulose-1-phosphate (Rham-1-P) Aldolase

As shown below in Scheme 5, Compounds VI, VII, VIII and IX from Scheme 3 can alternatively be condensed with DRAP in the presence of Rham-1-P aldolase (step a) to form azido-ketose-phosphate Compounds XXVI, XV, XVI and XVII, respectively. Compounds XIV, XV, XVI and XVII are then reductively cyclized by hydrogenation (step b) to yield azasugar Compounds 104, 105, 106 and 107, respectively. Rham-1-P Aldolase can be obtained from commercial sources (Sigma Chemical Co., St. Louis, Mo.) or isolated from *E. coli* strain K-40 (See Example 6 hereinafter).

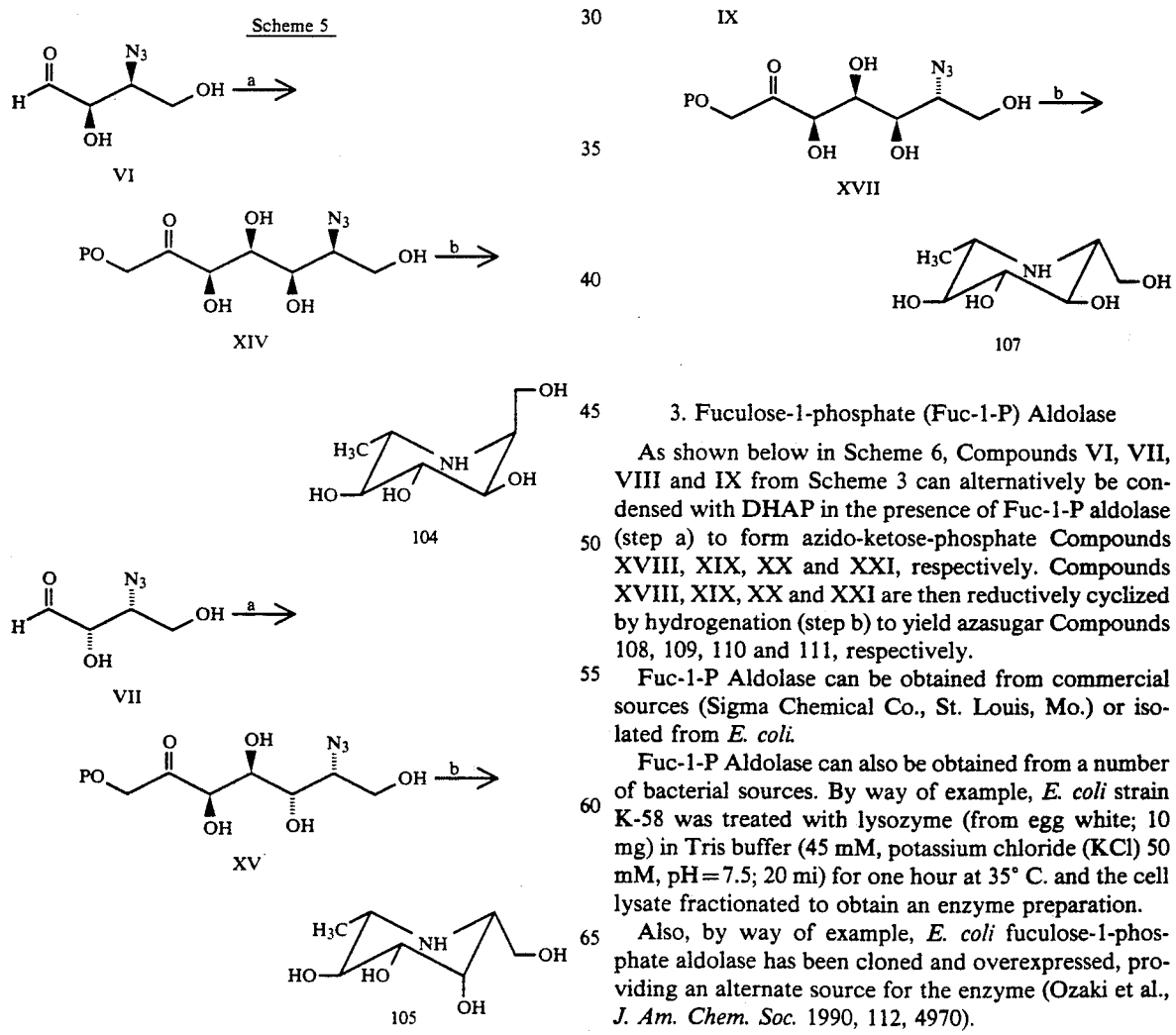

3. Fuculose-1-phosphate (Fuc-1-P) Aldolase

As shown below in Scheme 6, Compounds VI, VII, VIII and IX from Scheme 3 can alternatively be condensed with DHAP in the presence of Fuc-1-P aldolase (step a) to form azido-ketose-phosphate Compounds XVIII, XIX, XX and XXI, respectively. Compounds XVIII, XIX, XX and XXI are then reductively cyclized by hydrogenation (step b) to yield azasugar Compounds 108, 109, 110 and 111, respectively.

Fuc-1-P Aldolase can be obtained from commercial sources (Sigma Chemical Co., St. Louis, Mo.) or isolated from *E. coli*.

Fuc-1-P Aldolase can also be obtained from a number of bacterial sources. By way of example, *E. coli* strain K-58 was treated with lysozyme (from egg white; 10 mg) in Tris buffer (45 mM, potassium chloride (KCl) 50 mM, pH=7.5; 20 mi) for one hour at 35° C. and the cell lysate fractionated to obtain an enzyme preparation.

Also, by way of example, *E. coli* fuculose-1-phosphate aldolase has been cloned and overexpressed, providing an alternate source for the enzyme (Ozaki et al., *J. Am. Chem. Soc.* 1990, 112, 4970).

Scheme 6

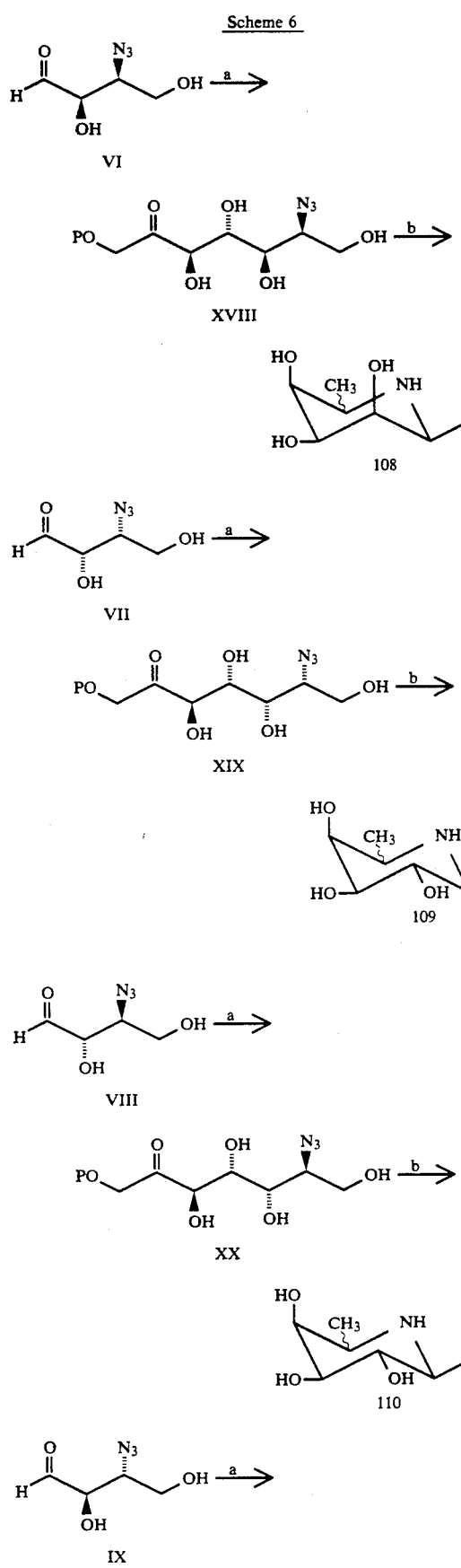

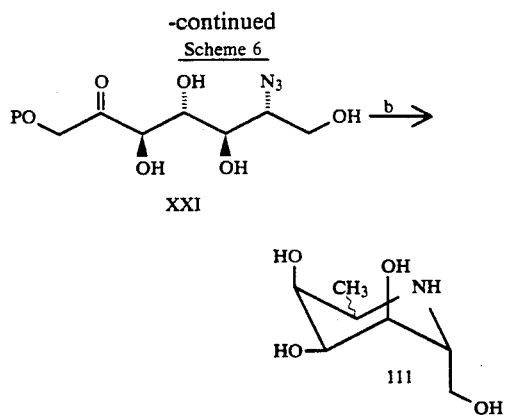

4. Tagatose-1,6-diphosphate (TDP) Aldolase

As shown below in Scheme 7, Compounds VI, VII, VIII and IX from Scheme 3 can alternatively be condensed With DHAP in the presence of TDP aldolase (step a) to form azido-ketose-phosphate Compounds XXII, XXXII, XXXV and XXV, respectively. Compounds XXII, XXIII; XXIV and XXV are then reductively cyclized by hydrogenation (step b) to yield azasugar Compounds 112, 113, 114 and 115, respectively. TDP Aldolase can be obtained from commercial sources (Sigma Chemical Co., St. Louis, Mo.) or isolated from bacteria *Lactococcus lactis* subsp. lactis.

Scheme 7

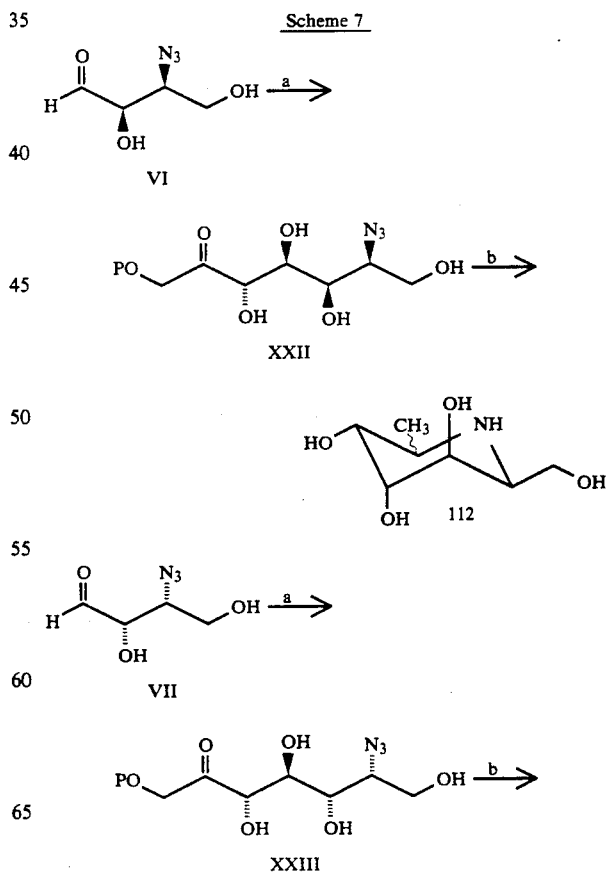

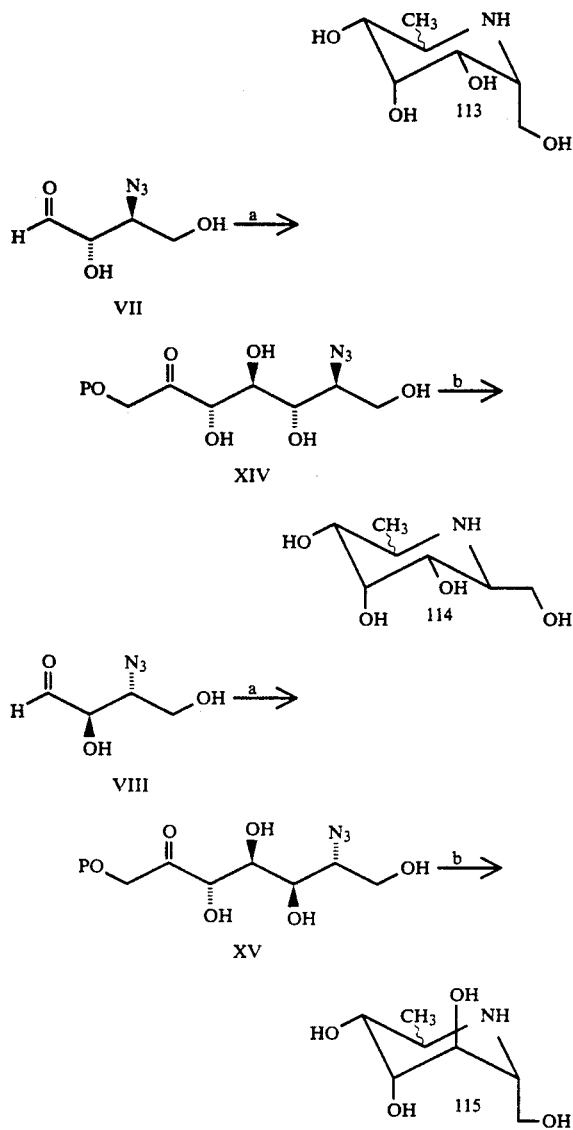

It can be seen from Schemes 4–7, above, that all sixteen isomers of an omega-deoxyazapyranose can be prepared by using aldolase catalyzed asymmetric aldol condensation and reductive cyclization by hydrogenation.

5. 2-Deoxyribose-5-phosphate Aldolase (DERA)

1,Omega-dideoxy-azapyranose compounds whose structures correspond to formula V, above, can conveniently be prepared from corresponding azido ketoses by a similar reductive cyclization to that noted above. Although the azido-substituted ketoses can be prepared by standard organic chemical procedures, again, enzymatic preparation is favored. Among the aldolases proven to be useful in organic synthesis is 2-deoxyribose-5-phosphate aldolase (DERA, EC 4.1.2.4), a 28,000 kD enzyme that reversibly catalyzes the condensation of acetaldehyde and D-glyceraldehyde 3-phosphate (D-G3P) to form 2-deoxyribose 5-phosphate (DRP). DERA is the only aldolase that accepts two aldehydes in the condensation reaction: other aldolases require a ketone and an aldehyde.

In addition to the donor substrate acetaldehyde and the wide variety of acceptors, DERA accepts at least two ketones as donor substrates, acetone and fluoroacetone, albeit at slower rates.

DERA expresses relaxed substrate specificities for both donor and acceptor components to form one (when acetaldehyde or acetone is the donor) or two (when propionaldehyde is used as donor) new stereogenic centers with 3S or 2R,3S-configurations. The acceptor substrates have very little structural requirements. The 2-hydroxyaldehydes appear to react the fastest, and the D-isomers are better substrates than the L-isomers. The stereospecificity is absolute regardless of the chirality of 2-hydroxy-aldehydes. The aldol reactions thus follow the Cram-Felkin mode of attack for D-substrates and anti-Cram-Felkin mode for L-substrates.

Thus, using 3-azido-2-hydroxypropanal as acceptor and acetaldehyde, acetone or propionaldehyde as donor, the appropriate azido aldose or ketose is formed from which a compound of formula V is prepared by reductive cyclization.

DERA can be obtained in recombinant form. For example, the overexpression of E. coli DERA has been achieved as a part of the cloned deo C system. Valentin-Hansen et al., EMBO J., 1:317 (1982). (See Example 19 hereinafter).

In a similar manner, 1,omega-dideoxy azapyranoses can be prepared by aldolase-catalyzed condensation and palladium-catalyzed reductive cyclization by hydrogenation.

The present synthesis of several omega-deoxy-azasugars and their derivatives began with the aldol condensation of 3-azido-2-hydroxypropanal and DHAP catalyzed by FDP aldolase, Rham-1-p aldolase, Fuc-1-p aldolase, TDP aldolase, or 3-azido-2-hydroxypropanal plus acetaldehyde, acetone, or propionaldehyde, in the case of DERA.

The addition of one of the above-mentioned aldolases to 3-azido-2-hydroxypropanal plus DHAP provided Compounds 1, 4 or 8 as are shown on the left side of Scheme 8, below. Both rhamnulose-1-phosphate aldolase and fuculose-1-phosphate aldolase accept the (S)-aldehyde as substrate, whereas FDP-aldolase is selective for the (R)-enantiomer [Pederson et al., Tetrahedron Lett, 1988, 29, 4645].

Palladium (Pd)-mediated reductive amination of phosphorylated Compounds 4 and 8 gave Compounds 6, 9 and 10 (at about a 1:1 ratio) respectively, each in approximately 90 percent total yield. In the same manner, the phosphorylated Compound 1c was hydrogenated directly to Compound 3c, also in high yield. These products are shown on the right side of Scheme 8.

Scheme 8

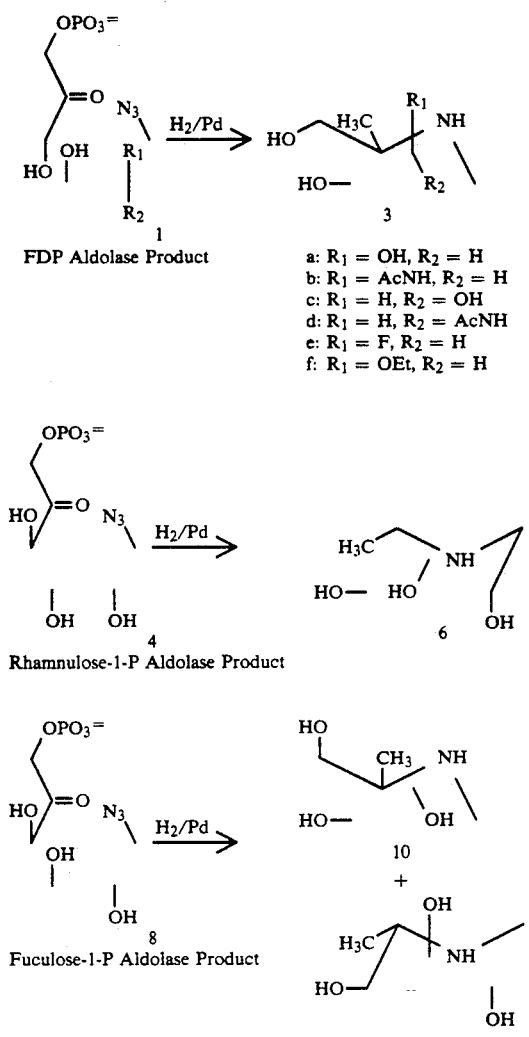

FDP Aldolase Product a: $R_1 = OH, R_2 = H$
b: $R_1 = AcNH, R_2 = H$
c: $R_1 = H, R_2 = OH$
d: $R_1 = H, R_2 = AcNH$
e: $R_1 = F, R_2 = H$
f: $R_1 = OEt, R_2 = H$ Rhamnulose-1-P Aldolase Product Fuculose-1-P Aldolase Product The synthesis of N-acetyl derivatives of an azasugar of Scheme 8, above, proceeds similarly from the reaction of DHAP with 3-azido-2-acetamidopropanal diethyl acetal, which is prepared from 3-azido-2-hydroxypropanal as described in Pederson et al., *J. Org. Chem.* 1990, 55, 4897. A key element in the synthesis of these N-acetyl dideoxy-azasugars is the preparation of Compound XXVI and its enantiomer as is shown in Scheme 9, below, and in which Roman numerals are used for intermediate compounds leading to the azido α-ketose phosphate.

Scheme 9

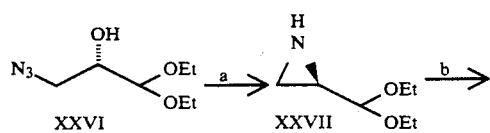

Scheme 9 -continued

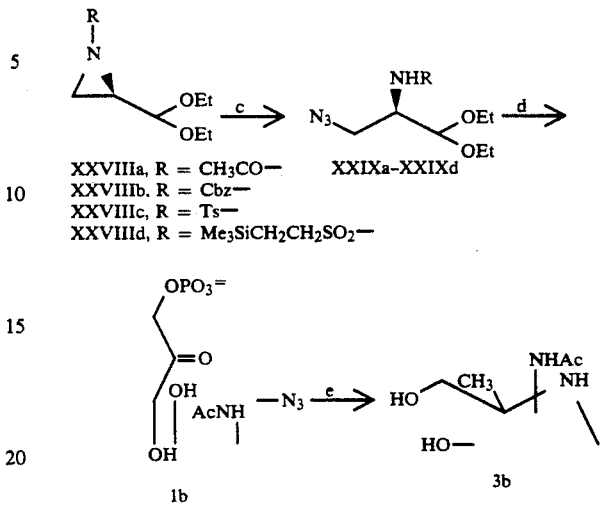

XXVIIIa, R = CH₃CO—
XXVIIIb, R = Cbz—
XXVIIIc, R = Ts—
XXVIIId, R = Me₃SiCH₂CH₂SO₂—

Thus, Compound XXVI (>98 percent ee) prepared previously [Von der Osten et al., *J. Am. Chem. Soc.* 1989, 111, 3924; Pederson et al., *Heterocycles* 1989, 28, 477] was converted to Compound XXVII [Pederson et al., *J. Org. Chem.* 1990, 55, 489] in step a, followed by N-acetylation to Compound XXVIIIA (95 percent ee). Nucleophilic opening of aziridine Compound XXVIIIA with sodium azide in the presence of zinc chloride (ZnCl₂) gave Compound XXIXA in 60 percent yield, in step c. The other protecting "R" groups are as shown in Scheme 9. Higher yields (75–86 percent) were obtained with other protecting groups (e.g. XXVIIIb-XXVIIId; Cbz=carbobenzoxy, Ts=p-toluenesulfonyl). The protecting group of Compound XXVIIId can be removed by F⁻ (Weinreb et al., *Tetrahedron Lett.* 1986, 2099].

Acid hydrolysis was used to unmask the aldehyde protecting group of Compound XXIXA. The unmasked product of Compound XXIXA (3 equivalents) was condensed with 1 equivalent of dihydroxyacetone phosphate (DHAP) in the presence of FDP aldolase at pH 6.5 to give Compound 1b (60 percent) in step d. Palladium catalyzed cyclization of Compound 1b provided Compound 3b, step e.

Compound 1d was prepared similarly from the enantiomer of Compound XXVI. Thus, starting with racemic Compound XXVI, a mixture of Compounds 3b and 3d in a 12:1 ratio was obtained.

Starting with enantiomerically pure aldehyde substrates, Compounds 3b and 3d were obtained separately.

The reductive aminations are all diastereoselective and consistent with the previous finding (von der Osten, C. H., et al. *J. Am. Chem. Soc.* 1989, 111, 3924) that hydrogen would attack the imine intermediate in a facial selective manner to avoid the torsional strain developed during the reduction (e.g., reactions with Compounds 1a–1f and Compound 4). An additional finding in this study is that hydrogen always approaches from the side opposite to the axial substituent (e.g., reactions with Compounds 1a, 1b, 1e, 4 and 8 and this stearic effect seems to override the torsional strain effect. The $A_{1,2}$ strain (e.g., Compounds 1 or 4) seems not to affect the stereochemical course of the reduction.

Compound 3c was N-methylated to give Compound 17. Similar alkylation with a longer alkyl group such as lauryl or butyl provides Compounds 20 and 21, respectively.

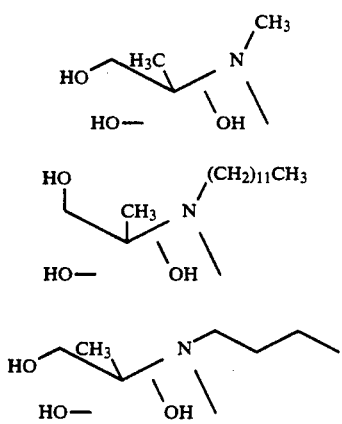

N-oxidation of Compound 17 with hydrogen peroxide ($H_2O_2$) resulted in a single stereoisomer with the N-methyl ($CH_3$) group at the equatorial position, as indicated, below, in Compound 18. Assignment of the stereochemistry was based on a strong nuclear Overhauser effect (NOE) observed between the various groups of a model compound.

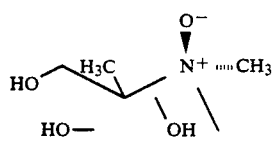

Synthesis of Compounds 14a–c also begins with 3-azido-2-hydroxypropanal, with formation of the precursor azaketose being catalyzed by DERA. DERA is unique in that it can catalyze the aldol condensation of two aldehydes. Therefore, in the case of Compound 14a the reactants were (RS)3-azido-2-hydroxypropanal and acetaldehyde to provide Compound 13a; Compound 14b was formed via the reaction of (RS)3-azido-2-hydroxypropanal and acetone to form Compound 13b; and Compound 14c was formed by reacting (RS)-3-azido-2-hydroxypropanal with propionaldehyde to form Compound 13c. None of the resulting azidoketoses or azidoaldoses contained phosphate groups, so reductive cyclization yielded Compounds 14a–c directly from parent Compounds 13a–c. Compounds 13a–c are shown below.

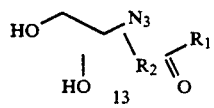

a: $R_1 = R_2 = H$
b: $R_1 = CH_3$, $R_2 = H$
c: $R_1 = H$, $R_2 = CH_3$

The synthesis of an exemplary 1,5-dideoxy-azasugar, (2R)-methyl-(5S)-hydroxymethyl-(3R,4R)-dihydroxypyrrolidine (Compound 25) is outlined below in scheme 10, in which Roman numerals are again used for the synthetic intermediates.

Scheme 10

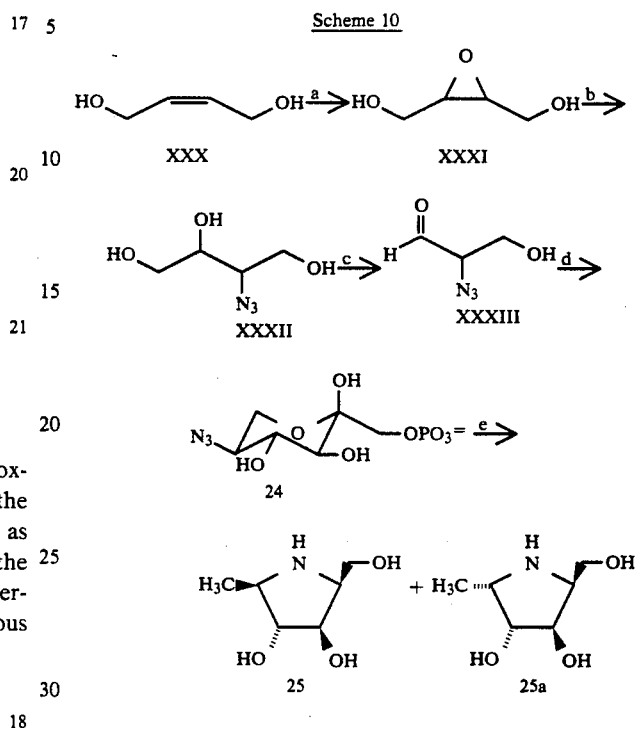

Thus, 1,4-dihydroxy-2-butene (Compound XXX) was oxidized to cis-2,3-epoxy-1,4-butanediol (Compound XXXI) in step a. The expoxide ring of Compound XXXI was nucleophilically opened in step b using sodium azide to form 2-azido-2-deoxy-threitol, Compound XXXII, (90 percent). Sodium periodate cleavage of Compound XXXII formed 2-azido-3-hydrypropanal, Compound XXXIII, in step c, which was not isolated.

Barium chloride was added to precipitate the formed periodite. The solution containing Compound XXXIII was adjusted to pH 7, then DHAP (0.5 equivalents) and FDP aldolase (from rabbit muscle, 500 Units) were added to the solution to form a reaction mixture. That reaction mixture was slowly stirred for two days to form the azido α-ketose phosphate Compound 24. Catalytic hydrogenation using Pd/C of Compound 24 in step e, gave Compound 25 and its 2S-diastereomer, Compound 25a, in 78 percent yield, with a 2R:2S ratio of about 6:1.

As set forth hereinbefore, the isomeric of configuration of azapyranoses made in accordance with the process of the present invention is dependent inter alia upon the particular aldolase used to condense DHAP and the azido aldehyde. In a similar manner, the isomeric of configuration azafuranoses made in accordance with that process is also dependent upon the particular aldolase enzyme. Thus, a variety of isomeric omega-deoxy azafuranoses can be made from DHAP and 2-azido-3-hydroxypropanal by using different aldolases as shown in Scheme 11, below. DHAP, 2-azido-3-hydroxypropanal and the azido-substituted α-ketose phosphate intermediate compound are not shown in Scheme 11 for purposes of clarity.

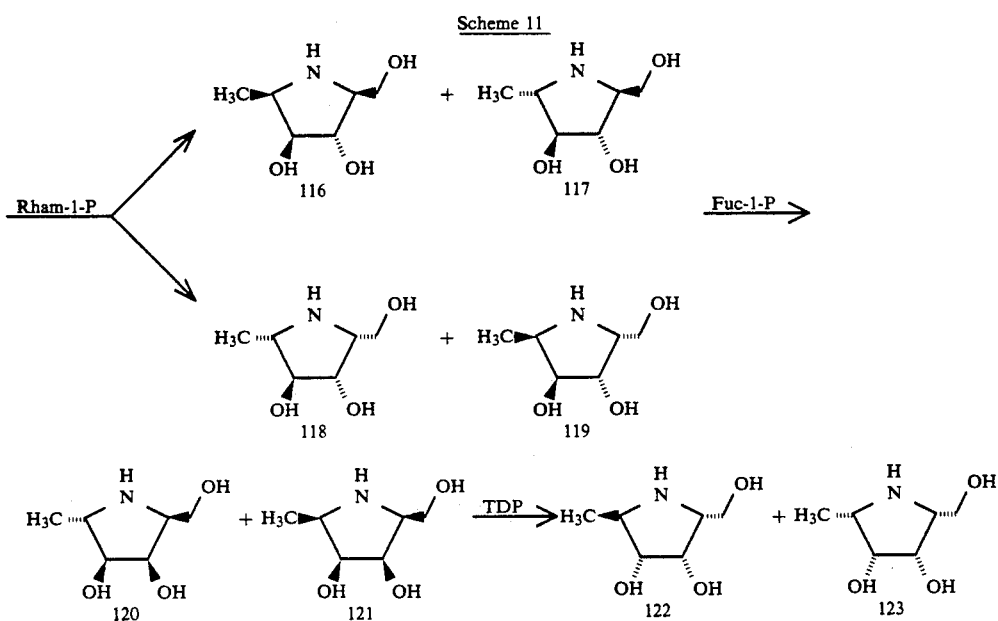

Scheme 11

1,Omega-dimethyl azafuranoses can be made in accordance with a process of the present invention using DHAP and 2-azido-propanal. The isomeric configuration of the 1,omega-dimethyl azafuranoses made in accordance with that process is also dependent inter alia upon the particular aldolase used to condense DHAP and the azido aldehyde. Thus, a variety of isomeric 1,omega-dimethyl azafuranoses can be made from DHAP and 2-azido-propanal by using different aldolases as shown in Scheme 12, below. DHAP, 2-azido-propanal and the azido-substituted α-ketose phosphate intermediate compound are not shown in Scheme 12 for purposes of clarity.

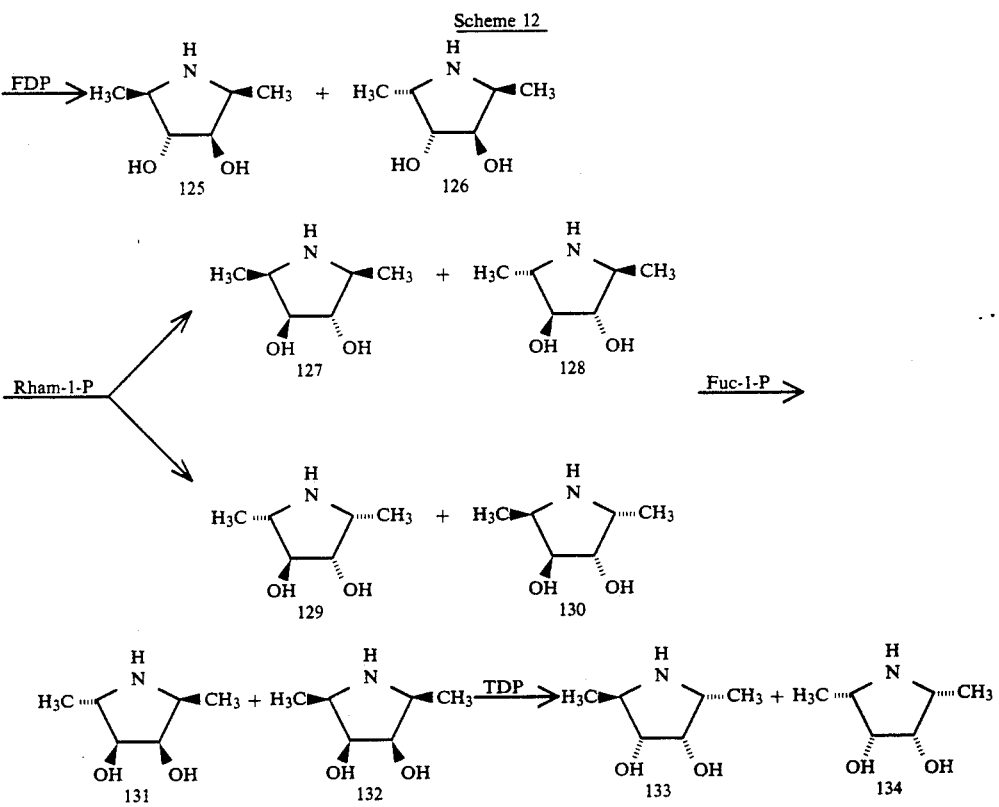

Scheme 12

By way of example, the condensation of DHAP and 2-azido-propanal in the presence of FDP aldolase yields, upon reductive cyclization by hydrogenation, diastereomeric Compounds 125 and 126.

The condensation of DHAP and 2-azido-propanal in the presence of Fuc-1-P aldolase yields, upon reductive cyclization by hydrogenation, diastereomeric Compound 131 and 132.

The condensation of DHAP and 2-azido-propanal in the presence of TDP aldolase yields, upon reductive cyclization by hydrogenation, diastereomeric Compounds 133 and 134.

Where DHAP and 2-azido-propanal are condensed in the presence of Rham-1-P aldolase, however, two pairs of diastereomeric products are formed. One pair, diastereomeric Compounds 127 and 128, is formed from a kinetically produced azido-substituted α-ketose phosphate intermediate compound. The other pair, diastereomeric Compounds 129 and 130, is formed from a thermodynamically produced azido-substituted α-ketose phosphate intermediate compound.

It can thus be seen that varying the type of aldolase enzyme used, a great variety of isomeric 1,omega-dimethyl azafuranoses can be made from a single ketone and single azidoaldehyde precursor.

A before-described omega-deoxy-azasugar is preferably also recovered once made. Recovery typically includes separation of the palladium catalyst from the reaction mixture used for reductive cyclization, followed by chromatographic or other separation of the formed dideoxy-azapyranose from any other materials present. Exemplary recoveries are provided hereinafter.

A $R^5$ group is added to a before-described azapyranose after reductive cyclization is completed. A $C_1$-$C_2$ alkyl group can be added by reductive alkylation of a corresponding aldehyde or ketone (See Example 19 hereinafter). A leaving group-substituted alkane can also be used for the alkylation. Exemplary leaving groups include halides, methanesulfonyl (mesyl) and p-toluenesulfonyl (tosyl) groups. Methods of N-alkylation are well known.

$C_1$-$C_{12}$ Acyl groups can be added via an appropriate anhydride or acid halide such as lauroyl chloride. Acylation methods are also well known.

N-Oxide derivatives are readily prepared from the N-alkyl derivatives by oxidation with hydrogen peroxide.

Compositions

Also contemplated by this invention is a composition that comprises a glycosidase-inhibiting amount of a before-described omega-deoxy-azapyranose dispersed in an aqueous medium. Preferably, the aqueous medium is a pharmaceutically acceptable, non-toxic medium such as normal saline, phosphate-buffered saline, Ringer's solution or the like as are well known in the art. The aqueous medium can also comprise blood, serum, plasma or lymph of a mammal such as a mouse, rat, rabbit, guinea pig, dog or human to which the azapyranose is administered.

A glycosidase-inhibiting amount is an amount that inhibits a preselected glycosidase enzyme by at least 25 percent, more preferably by about 50 percent, and most preferably by about 75 percent or more. The data herein provide concentrations ($K_i$) at which 50 percent inhibition is observed in vitro for several specific glycosidases. Those $K_i$ values can be utilized as a starting concentration range for determining inhibitory concentrations in other enzymes, using standard laboratory screening procedures such as Lineweaver-Burk plots.

A before-described azapyranose is dispersed in the aqueous medium. Such dispersal includes suspensions as well as true solutions, which are ultimate dispersions, in the aqueous medium. Thus, for example, the long chain alkyl and acyl groups that can be present as an $R^5$ group tend to lessen water-solubility while enhancing lipid solubility.

The following examples are intended to illustrate the invention and not limit it.

Example 1.
(2R)-methyl-(3S,4R,5S)-trihydroxypiperidine; (1,5,6-Trideoxy-1,5-imino-D-glucitol), Compound 3c A solution of (R)-3-azido-2-hydroxypropanal diethyl acetal (Compound XXVI; 480 milligrams (mg), 2.54 millimoles (mmol)) in 10 milliliters (mL) of a hydrogen chloride (HCl; pH 1) buffer solution was stirred at 70° C. for four hours. Gas chromatography analysis [J&W Scientific DB-5 column (15 m×0.522 Mm), 40° C. for one minute to 250° C. at 20° C./minute] showed complete hydrolysis of the acetal (retention time of starting material 6.33 minutes, corresponding aldehyde 2.65 minutes). The solution was adjusted to pH 7, then DHAP (2 mmol) was added and the solution readjusted to pH 7. Rabbit muscle FDP aldolase (400 units) was then added, and the solution was stirred slowly for 36 hours. Enzymatic assay showed no DHAP remaining.

Barium chloride ($BaCl_2.2H_2O$) [1.22 grams (g), 4.80 mmol] and two equivalent volumes of acetone were added to the solution. The solution was maintained at $-20°$ C. for about 18 hours. The precipitate was recovered, and treated with Dowex X 50($H^+$) in 20 mL water to remove barium cation. After filtration, the solution was adjusted to pH 7 and then lyophilized to obtain Compound 1c (550 mg, 1.79 mmol, 90% based on DHAP) as a white hygroscopic solid: $R_f$=0.46 [2-propanol: ammonium hydroxide ($NH_4OH$):-$H_2O$=6:3:2]; $^1$H-NMR ($D_2O$) δ 3.36 (1H, dd, J=13.25, 5.88 Hz) , 3.48 (1H, dd, J=13.25, 3.28 Hz), 3.68-3.89 (1H, m), 4.03-4.07 (1H, 4.25-4.33 (1H, m) ppm; $^{13}$C-NMR ($D_2O$) δ: 50.65, 66.35, 74.82, 76.32, 79.96, 101.25 (d, J=8.5 Hz) ppm. HRMS ($M+H^+$) calculated 307.1319, found 307.1321.

A solution of Compound 1c (550 mg, 1.79 mmol) in 10 mL of water was hydrogenated with 50 mg 10 percent palladium/carbon catalyst (Pd/C) under 45 pounds per square inch (psi) of hydrogen ($H_2$) for 18 hours. The catalyst was removed by filtration and the filtrate was concentrated and chromatographed on a short silica gel column [chloroform ($CHCl_3$): methanol (MeOH): $H_2O$ = 5:5:2] to yield the title compound, Compound 3c (250 mg, 95 percent) as a white fluffy compound: $R_f$=0.60 (2-propanol: $NH_4OH$: $H_2O$=6:3:2); $[\alpha]_D^{23}$ +12.0° (c 2.5, $H_2O$); $^1$H-NMR ($D_2O$) δ 1.10 (3H, d, J=6.4 Hz, $CH_3$), 1.27 (3H, d, J=6.8 Hz, 5-epimer-$CH_3$), 2.48 (1H, t, $J_{1a,1e}=J_{1a,2}=12$ Hz, H-1a), 2.63 (1H, dd, $J_{5,6}$=6.4, $J_{5,4}$=3.6 Hz, H-5), 3.03 (1H, t, $J_{3,4}=J_{4,5}$=9 Hz, H-4), 3.47-3.52 (1H, m, H-2) ppm; $^{13}$C-NMR ($D_2O$) δ 16.82, 48.22, 55.76, 69.98, 75.37, 77.83 ppm. HRMS ($M+H^+$) calculated 148.1001, found 148.0979.

Example 2.
(2R)-methyl-(3S,4R,5R)-trihydroxypiperidine; (1,5,6-Trideoxy-1,5-imino-D-mannitol), Compound 3a A solution of (S)- or (RS)-3-azido-2-hydroxypropanal diethyl acetal (480 mg, 2.54 mmol) in 10 mL of the pH 1 buffer solution was stirred at 70° C. for four hours. Gas chromatography analysis (J&W Scientific DB-5 column (15 m×0.522 Mm), 40° C. for one minute to 250° C. at 20° C./minute) showed complete hydrolysis of the acetal (retention time of starting material 6.33 minutes, corresponding aldehyde 2.65 minutes). The solution was adjusted to pH 7. then DRAP (2 mmol) was added and the solution readjusted to pH 7. Rabbit muscle FDP aldolase (400 units) was then added, and the solution was stirred slowly for 36 hours. Enzymatic assay showed no DHAP remaining.

Barium chloride ($BaCl_2.2H_2O$) (1.22 g, 4.80 mmol) and two equivalent volume of acetone were added to the solution. The solution was maintained at $-20°$ C. for about 18 hours. The precipitate was recovered, and treated with Dowex X 50($H^+$) in 20 mL water to remove barium cation. After filtration, the solution was adjusted to pH 7 and then lyophilized to obtain the phosphorylated azidoketose.

A solution of this azido α-ketose phosphate in 10 mL of water was hydrogenated with 50 mg 10 percent Pd/C under 45 psi of hydrogen for 18 hours. The catalyst was removed by filtration and the filtrate was concentrated and chromatographed on a short silica gel column ($CHCl_3$:MEOH:$H_2O$ = 5:5:2) to yield the title compound, Compound 3a: $R_f$=0.12 ($CHCl_3$:MeOH:$H_2O$ =5:5:1.5); $[\alpha]_D^{23}-4°$ (c=2.5, $H_2O$); $^1$H-NMR ($D_2O$) δ: 1.213 (3H, d, J=6.5 Hz, $CH_3$), 2.893 (1H, dd, $J_{4,5}$=9.5 Hz, $J_{5,6}$=6.5 Hz, H-5), 3.00 (1H, d, $J_{1a,1e}$=13.5 Hz, H-1a), 3.16 (1H, dd, $J_{1e,1a}$=13.5 Hz, $J_{1e,2}$=3 Hz, H-1e), 3.45 (1H, t, $J_{1e,2}$=3 Hz, H-2), 3.46 (1H, t, J=9.5 Hz, H-4), 3.675 (1H, dd, $J_{3,4}$=9.5 Hz, $J_{2,3}$=3 Hz, H-3) ppm; $^{13}$C-NMR ($D_2O$) δ: 15.24 ($CH_3$), 48.31(C-1), 56.17(C-5), 66.74, 70.88, 72.92 ppm. HRMS ($M+H^+$) calculated 148.0974, found 148.0900.

Example 3.
(2R)-Methyl-(3R,4R)-(5R)-N-acetylpiperidine; (1,5,6-trideoxy-1,5-imino-N-acetylglucosamine; Compound 3b), and
(2R)-methyl-(3R,4R)-dihydroxy-(5S)-N-acetylpiperidine; (1,5,6-trideoxy-1,5-imino-N-aceytylmannosamine; Compound 3d)

To a mixture containing 100 mL of dichloromethane ($CH_2Cl_2$), 5.27 g (36.3 mmol) of (R)-2-(diethoxymethyl)aziridine (Compound XXVII, 95 percent ee) and 40.0 g (289.4 mmol) of dipotassium carbonate ($K_2CO_3$) were added 4.0 mL (42.4 mmol) of acetic anhydride. The mixture was stirred at room temperature for 10 hours, filtered, and the solvent was removed under reduced pressure. The residue was purified by silica gel column chromatography to yield 4.27 g of Compound XXVIIIa: 63 percent yield; $[\alpha]_D^{23}+84.23°$ (c 1.5, $CHCl_3$) $^1$H-NMR ($CDCl_3$) δ 1.22, 1.25 (each 3H, t, J=7.0 Hz, $CH_2CH_3$), 2.17 (3H, s, $CH_3CO$), 2.28 (1H, d, J=3.3 Hz, $CH_2$ of aziridine) 2.35 (1H, d, J=6 Hz, $CH_2$ of aziridine), 2.68 (1H, m, CH of aziridine), 3.51-3.78 (4H, m, $OCH_2$), 4.40 (1H, d, J=4.5 Hz, $CH(OEt)_3$) ppm; $^{13}$C-NMR ($CDCl_3$) δ 15.6 (2C), 23.8, 27.7, 38.3, 63.2, 63.3, 101.6, 183.2 ppm. HRMS ($M+H^+$) calculated 188.1286, found 188.1290.

Compounds XXVIIIb, XXVIIIE and XXVIIId were similarly prepared using appropriate blocking groups.

To a mixture containing 423.0 mg (2.26 mmol) of Compound XXVIIIa and 1.9 g (29.5 mmol) of sodium azide in 18 mL of dimethyl fluoride (DMF) were added 18.0 mL of zinc chloride [1.0 molar (M) solution in ether], and the reaction mixture was stirred at 75° C. for three days. The mixture was extracted with ethyl acetate (EtOAc) and the organic layer was washed with water, dried over magnesium sulfate ($MGSO_4$) and concentrated. The residue was purified by silica gel chromatography (hexane:EtOAc=3:2) to yield 318.6 mg of Compound XXIXa [61 percent yield, $[\alpha]_D^{23}-23.8°$ (c 0.15, $CHCl_3$)]. $^1$H-NMR ($CDCl_3$) δ 1.23 (6H, t, J=7.1 Hz, $CH_2CH_3$), 2.03 (3H, s, $CH_3CO$), 3.45-3.61 and 3.66-3.76 (6H, m), 4.24 (1H, m, —CHNH), 4.53 (1H, d, J=3.9 Hz, —CH(OEt)$_3$), 5.83 (1H, d, J=7.8 Hz, —NH) ppm; $^{13}$C-NMR ($CDCl_3$) δ 15.5, 15.6, 23.7, 50.8, 51.0, 63.7, 64.4, 101.3, 170.5 ppm. HRMS ($M+Cs^+$) calculated 363.0433, found 363.0450.

The aldehyde liberated from racemic Compound XXIXa (1 g) was mixed with 18 mL of DHAP (71.3 mmol), and the pH was adjusted to 6.5 with 1 normal (N) sodium hydroxide (NaOH). To this solution, rabbit muscle FDP aldolase (400 units) was added, and the mixture was stirred slowly for 4.5 hours. The mixture was passed through Dowex 1 ($HCO_2$—) and eluted with water (400 ml) 0.1 molar (M) sodium chloride (NaCl; 250 mi), 0.4M NaCl (700 mL), and 0.5M NaCl solution, successively.

After adding 200 ML of water to the fraction eluted by the 0.4M NaCl solution (700 mL) that contained Compound 1b, Pd/C (103.0 mg) was added, and the mixture was hydrogenated under the pressure of 50 psi for one day. The catalyst was filtered off and the filtrate was lyophilized. The residue was treated with a mixed solvent [chloroform ($CHCl_3$):methanol (MEOH):$H_2O$=6:4:1]. The soluble portion was collected and purified by silica gel chromatography ($CHCl_3$:MeOH:$H_2O$=6:4:0.7) to yield Compounds 3b and 3d in a 12:1 ratio. Starting with enantiomerically pure aldehyde substrates, Compounds 3b and 3d were separately obtained. Compound 3b: $^1$H-NMR ($D_2O$) δ: 1.33 (3H, d, J=6.3 Hz, H-6), 1.94 (3H, s, $CH_3CO$), 2.85 (1H, t, J 12.5 Hz, H-1a), 3.10 (1H, m, H-5), 3.36 (1H, dd, J 12.5 and 4.9 Hz, H-1e), 3.39, 3.51 (each 1H, t, J=9.8 Hz, H-3,4), 3.99 (1H, ddd, J=12.5, 9.8 and 4.9 Hz, H-2) ppm; $^{13}$C-NMR ($D_2O$) δ: 14.8, 22.3, 44.0, 48.2, 54.9, 72.9, 73.1, 174.2 ppm. HRMS ($M+Na^+$) calculated 211.1059, found 211.1053. Compound 3d: $^1$H-NMR (DO) δ: 1.34 (3H, d, J=6.6 Hz, H-6), 1.97 (3H, s, $CH_3CO$), 3.10 (1H, m, H-5), 3.15, 3.43 (each 1H,dd, J=13.7 and 3.0 Hz, H-1), 3.62 (1H, t, J=9.4 Hz, H-4), 3.80 (1H, dd, J=9.4 and 4.6 Hz, H-3), 4.32 (1H, dt, J=4.6 and 3.0 Hz, H-2) ppm; $^{13}$C-NMR ($D_2O$) δ: 14.5, 22.4, 44.4, 47.6, 55.0, 69.9, 70.0, 174.7 ppm. HRMS ($M+Na^+$) calculated 211.1059, found 211.1050.

Example 4.
(1,2R)-dimethyl-(3R,4R,5S)-trihydroxypiperidine; (N-Methyl-1,5,6-trideoxy-1,5-imino-D-glucitol), Compound 17

A solution containing Compound 3c (47 mg, 0.32 mmol), formaldehyde (300 ml, 37 percent by weight solution) and 10 mg of 10 percent Pd/C was hydrogenated under 45 psi of hydrogen in 10 mL of MeOH/$H_2O$ (1:1) solution for one day. After filtration, the solvent was removed under reduced pressure to yield Compound 17 (52 mg, quantitative yield) as hygroscopic material: $R_f$=0.65 (2-propanol:$NH_4OH$:$H_2O$=6:3:2) ; $[\alpha]_D^{23}+4.58°$ (c 1.75, $H_2O$); $^1$H-NMR ($D_2O$) δ 1.12 (3H, d, J=6.5 Hz) , 2.36 (1H, dd, J=11.5, 6.5 Hz), 2.63 (1H, d, J=5 Hz), 3.02-3.06 (2H, m), 3.18 (1H, t, J=9.5 Hz), 3.48-3.53 (1H, m) C-NMR ($D_2O$) δ 16.96, 43.87, 61.17, 65.96, 70.68, 76.64, 79.95 ppm. HRMS ($M+H^+$) calculated 161.1052, found 162.1129.

Example 5.
(1,2R)-dimethyl-(3R,4R,5S)-trihydroxypiperidine oxide; (N-Methyl-1,5,6-trideoxy-1,5-imino-D-glucitol oxide), Compound 18

Hydrogen peroxide (42 mg, 50 percent by weight solution) was added to a 1 mL H$_2$O solution containing Compound 17 (10 mg, 0.062 mmol) and the mixture was stirred at room temperature for 3 days. The solvent was removed under reduced pressure to obtain pure Compound 18 (10 mg, 91%) as a single stereoisomer of white hygroscopic compound: R$_f$=0.53 (2-propanol:N-H$_4$OH:H$_2$O=6:3:2); [α]$_D^{23}$+5.40° (c 3.00, H$_2$O); $^1$H-NMR (D$_2$O) δ 1.12 (3H, d, J=6.5 Hz, CH$_3$), 3.14 (1H, dd, J$_{5,4}$=10, $^J$5, CH$_3$=6.5 Hz, H-5), 3.20 (1H, t, J$_{2,3}$=J$_{3,4}$=10 Hz, H-3), 3.28 (1H, t, J$_{1a,1e}$=J$_{1a,2}$=10 Hz, H-1a), 3.39 (1H, dd, J$_{1e,1a}$=10, J$_{1e,2}$=5 Hz, H-1e), 3.41 (1H, t, J$_{3,4}$=J$_{4,5}$=10 Hz, H-4), 3.88 (1H, td, J$_{1a,2}$=J$_{23}$=10, J$_{2,1e}$=5 Hz, H-2) ppm; $^{13}$C-NMR (D$_2$O) δ 8.65, 55.89, 67.85, 64.52, 70.21, 70.60, 75.44 ppm. HRMS (M+H$^+$) calculated 177.2009, found 177.2014.

Example 6.
(2S)-methyl-(3S,4S,5S)-trihydroxypiperidine; [1,6-L-rhamnanojirimycin (rhamnojirimycin)], Compound 6

To an aqueous solution of (RS) or (R)-3-azido-2-hydroxypropanal, prepared by heating a suspension of 3-azido-2-hydroxypropanal diethyl acetal (1.1 g, 5.8 mmol) in pH 1.0 buffer (40 mL) at 45° C. for 12 hours, were added DHAP (1.9 mmol) and Tris buffer (675 mM, KCl 750 mM, pH=7.5; 5.0 mL), and the pH value of the resulting solution was adjusted to 7.5 with 1N NaOH. To prepare a source for rhamnulose-1-phosphate aldolase, E. coli strain K-40 was treated with lysozyme (from egg white; 10 mg) in Tris buffer (45 mM, potassium chloride (KCl) 50 mM, pH=7.5; 20 mL) for 1 hour at 35° C. One gram of this E. coli preparation was added to the above pH-adjusted solution, and the mixture was stirred slowly until 90 percent of DHAP was consumed.

After the reaction, the solution was adjusted to pH 7.0, BaCl$_2$.2H$_2$O (950 mg, 3.9 mmol) was added, and the resulting precipitate was removed by centrifugation. Acetone (twice the volume) was added to the supernatant. The mixture was kept in a refrigerator for two hours and the precipitate newly appeared was collected. To remove the barium ion, Dowex 50 (H+) was added with stirring followed by filtration. The solution was lyophilized and the residue was purified by silica gel chromatography (CHCl$_3$:MeOH:H$_2$O=8:2:0.1) to yield the phosphorylated azidoketose, Compound 4.

Compound 4 in ethanol (30 mL) containing Pd/C (20 mg) was hydrogenated at 50 psi for one day. The catalyst was filtered off and the filtrate was concentrated. The residue was purified by silica gel chromatography (CHCl$_3$: MeOH: H$_2$O=6:4:1~5:5:2) to yield Compound 6.

Compound 4a (dephosphorylated): Yield 55 percent (based on DHAP), $^{13}$C-NMR (CD30D) δ 54.6, 64.2, 76.8, 77.6, 81.1, 103.3 ppm.

Compound 6: $^1$H-NMR (D$_2$O) δ 1.00 (3H, d, J=6.5, 5-CH$_3$), 2.30 (1H, m, H-5), 2.56 (1H, d, J=14.4, H-1a), 2.78 (1H, dd, J=14.4, 2.3, H-1e), 3.14 (1H, t, J=9.9, H-4), 3.35 (1H, dd, J=9.9, 2.9, H-3), 3.82 91H, bs, H-2) ppm; $^{13}$C-NMR (D$_2$O) δ 17.4, 48.6, 55.6, 69.8, 74.3, 74.5 ppm. HRMS (M+Cs$^+$) calculated 279.9950, found 279.9950.

Example 7.
(2R)-Methyl-(3S,4R,5S)-trihydroxypiperidine; (D-1,6-D-dideoxygalactojirimycin), and (2S)-methyl-(3S,4R,5S)-trihydroxypiperidine; (L-1,6-dideoxyaltrojirimycin), Compounds 9 and 10

To an aqueous solution of (RS)- or (R)-3-azido-2-hydroxypropanal, prepared by heating a suspension of 3-azido-2-hydroxypropanal diethyl acetal (1.1 g, 5.8 mmol) in pH 1.0 buffer (40 mL) at 45° C. for 12 hours, were added DHAP (1.9 mmol) and Tris buffer (675 mM, KCl 750 mM, pH=7.5; 5.0 mL), and the pH was adjusted to 7.5 with 1N NAOH. To prepare a source for fuculose-1-phosphate aldolase, E. coli strain K-58 was treated with lysozyme (from egg white; 10 mg) in Tris buffer (45 mM, potassium chloride (KCl) 50 mM, pH=7.5; 20 mL) for one hour at 35° C. One gram of this E. coli preparation was added to the above ph-adjusted solution, and the mixture was stirred slowly until 90 percent of DHAP was consumed. E. coli fuculose-1-phosphate aldolase has been cloned and overexpressed, providing an alternate source for the enzyme (Ozaki et al., J. Am. Chem. Soc. 1990, 112, 4970).

After the reaction, the solution was adjusted to pH 7.0, BaCl$_2$.2H$_2$O (950 mg, 3.9 mmol) was added, and the resulting precipitate was removed by centrifugation. Acetone (twice the volume) was added to the supernatant. The mixture was kept in a refrigerator for two hours and the precipitate newly appeared was collected. To remove the barium ion, Dowex 50 (H+) was added with stirring followed by filtration. The solution was lyophilized and the residue was purified by silica gel chromatography (CHCl$_3$:MEOH:H$_2$O=8:2:0.1) to yield a phosphorylated azidoketose, Compound 8, in 20 percent (based on DHAP). Compound 8: $^{13}$C-NMR (CD$_3$OD) δ 52.7, 66.7, 71.9, 72.8, 80.1, 104.4 ppm.

A solution of compound 8 in ethanol (30 mL) containing Pd/C (20 mg) was hydrogenated at 50 psi for one day. The catalyst was filtered off and the filtrate was concentrated. The residue was purified by silica gel chromatography (CHCl$_3$:MeOH:H$_2$O=6:4:1~5:5:2) to yield an approximately equimolar mixture of Compounds 9 and 10. Compound 10: [α]$_D$+18.2° (c 1.1,MEOH), $^1$H-NMR (D$_2$O) δ 1.20 (3H, d, J=6.7, 5-CH$_3$), 2.71 (1H, t, J=12.0, H-1a), 3.30 (1H, qd, J=6.7, 1.5, H-5), 3.31 (1H, dd, J=12.0, 5.5, H-1e), 3.50 (1H, dd, J=9.7, 3.0, H-3), 3.87 (1H, dd, J=3.0, 1.5, H-4), 3.90 (1H, ddd, J=11.5, 9.5, 5.5 Hz, H-2) ppm; $^{13}$C-NMR (D$_2$O) δ 14.4, 46.5, 55.3, 64.8, 70.3, 73.5 ppm. HRMS (M+H$^+$) calculated 148.0974, found 148.0974.

Example 8.
(2R)-Methyl-2-fluoro-(3R,4R,5R)-trihydroxypiperidine; (2,6-Dideoxy-2-fluormannojirimycin), Compound 3e To a stirring solution of 3-azido-2-hydroxypropanal diethyl acetal (7.32 g, 38.73 mmol) in dry benzene (50 mL) was added diethylaminosulfurtrifluoride (DAST; 20.6 mL) at −78° C. After the addition, the solution was stirred at room temperature for an hour, then heated to 70° C. for 12 hours. The reaction was quenched by the addition of methanol at zero degrees C. and dilution with water. After dichloromethane extraction, the organic layer was dried over MgSO$_4$ and concentrated in vacuo. The crude product was purified with silica gel column chromatography (hexane: ether=9:1, volume/volume) to yield 3-azido-2-fluoropropanal diethyl acetal as an oil (65 percent); R$_f$=0.84

EtOAc:hexane=2:3) $^1$H-NMR (CD$_3$Cl) δ 1.215~1.219 (6H, m) 3.526 (2H, dm, J=15.3 Hz), 3.642~3.670 (2H, m), 3.680~3.808 (2H, m), 4.514 (1H, dm, J=45.9 Hz) ppm.

A mixture of racemic 3-azido-2-fluoropropanal diethyl acetal (750 mg, 3.93 mmol) and 1N HCl (20 mL) was heated at 65° C. for 30 hours. The mixture was cooled to room temperature and DHAP (1 mmol) was added, and the pH value was adjusted to 7 with 10N NAOH. Rabbit muscle FDP aldolase (500 Units) was added to the pH-adjusted solution and the resulting solution was stirred slowly for 36 hours. Enzymatic determination indicated that all of the DRAP had been consumed. The solution was then filtered and lyophilized. The yellow syrup was treated with water and filtered to remove the insoluble material. The water was removed under reduced pressure to provide Compound 1e.

A solution containing this product (20 mg) and 10 percent Pd/C (5 mg) in 10 mL H$_2$O was hydrogenated at 50 psi for one day. The catalyst was filtered off and the solvent was removed under reduced pressure. The crude product was purified by silica gel column chromatography (CHCl$_3$:MeOH=3:1) to yield 2,6-dideoxy-2-fluormannojirimycin, Compound 3e.

Example 9. (3S,4S)-dihydroxypiperidine, Compound 14a; (3R,4R)-dihydroxy-(6R)-methypiperidine, Compound 14b; (3S,4S)-dihydroxy-(5R)-methypiperidine, Compound 14c To a 10 mL solution containing 100 Mm D-(R)-3-azido-2-hydroxypropanal, 300 mM acetone, 100 Mm triethanolamine buffer, pH 7.3, and 1 mM EDTA, 400 units of DERA was added. The resulting solution was stirred in the dark for 2 days under N$_2$. The reaction was quenched by addition of 2 volumes acetone. The mixture was then incubated in ice for 20 minutes and centrifuged to remove the precipitated enzyme. After removal of the solvent under reduced pressure, the residue was purified by silica gel chromatography (ethyl acetate:hexane, 2:1, R$_f$ 0.12) to give Compound 13b in 66% yield.

$^1$H NMR (D$_2$O) of major anomer d 2.24 (s, 3H, CH$_3$), 2.68 (dd, J =9.2, 16.6, 1H, H-3), 2.89 (dd, J=3.4, 16.6, 1H, H-3), 3.40 (dd, J=7.0, 13.1, 1H, H-6), 3.52 (dd, J=3.1, 13.1,1H, H-6), 3.69 (dt, J=3.1, 6.9, 1H, H-5), 4.07 (ddd, J=3.1, 6.8, 7.0, 1H, H-4). $^{13}$C NMR (D$_2$O) d 28.4 (C-1), 45.0 (C-3), 51.3 (C-6), 66.6, 71.4 (C-4, C-5), 88.3 (C-2). HRMS (M-Cs)$^+$ Calcd 305.9855, found 305.9871.

Compound 13b was recovered and hydrogenated over Pd/C as described above to provide Compound 14b.

Compound 14b: $^1$H-NMR (CDCl$_3$) δ 1.05 (3H, d, J=6.3, H-1), 1.27 (1H, q, J=12.4, H-3a), 1.67 (1H, ddd, J=12.5, 4.7, 2.5, H-3e), 2.55 (1H, ddq, 12.6, 6.3, 2.5, H-2), 2.62 (1H, dd, J=13.4, 1.3, H-6a), 3.06 (1H, dd, J=13.4, 2.9, H-6e), 3.25 (3H, br s, 2OH, NH), 3.53 (1H, ddd, J=11.9, 4.7, 3.0, H-4), 3.69 (1H, br s, H-5) ppm; $^{13}$C-NMR (CDCl$_3$) 6 22.1 (C-1), 37.7 (C-3), 50.1, 50.5 (C-2, C-6), 67.2 69.9 (C-4, C-5) ppm. HRMS (M+Cs$^+$): Calculated 264.0001, found 264.0000.

To a 10 mL solution containing 100 Mm D-(R)-3-azido-2-hydroxypropanal, 300 Mm propanol, 100 Mm triethanolamine buffer, pH 7.3, and 1 Mm EDTA, 400 units of DERA was added. The resulting solution was stirred in the dark for 2 days under N$_2$. The reaction was quenched by addition of 2 volumes acetone. The mixture was then incubated in ice for 20 minutes and centrifuged to remove the precipitated enzyme. After removal of the solvent under reduced pressure, the residue was purified by silica gel chromatography (ethyl acetate:hexane, 2:1, R$_f$ 0.12) to give Compound 13c in 20% yield.

$^1$H NMR (D$_2$O) of β form: δ 1.02 (d, J=7.2, 3H,CH$_3$) 2.17 (1H, m,1H,H-2), 3.39 (dd, J=7.1, 13.2, 1H, H-5), 3.49 (dd, J=3.2, 13.2, 1H, H-5), 3.65 (ddd, J=3.2, 5.7, 7.1, 1H, H-4), 4.22 (dd, J=3.6, 6.1, 1H, H-3), 5.14 (d, J=5.1,1H, H-1). α form: δ 1.02 (d, 3H, CH$_3$), 2.28 (m, 1H, H-2), 3.39 (dd, J=6.6, 13.2, 1H, H-5), 3.5 (dd, J=4.5, 13.2,1H, H-5), 4.01 (dt, J=3.9, 6.7, 1H,H-4). 4.08 (dd, J=2.1, 6.2,1H, H-3), 5.39 (d, J=5.0, 1H, H-1). $^{13}$C NMR (D$_2$O) δ 7.4 (CH$_3$) 42.4 (C-2), 51.1 (C-5), 72.4 (C-3), 81.6 (C-4), 102.4 (C-1). HRMS (M+Cs$^+$) Calcd 305.9855, found 305.9871.

Compound 13c was recovered and hydrogenated over Pd/C as described above to provide Compound 14c.

Compound 14c: $^1$H-NMR (D$_2$O) 6 0.91 (3H, d, J=7.0, CH$_3$), 1.77-1.82 (1H, m, H-2), 2.45 (1H, t, J=12.4, H-1a), 2.67 (1H, t, J=11.7, H-5a), 2.70 (1H, dd, J=12.4, 4.8, H-1e), 2.90 (1H, dd, J=11.9, 4.6, H-5e), 3.72 (1H, ddd, J=11.7, 5.1, 3.0, H-4), 3.85 (1H, br s, H-3) PPM; $^{13}$C-NMR (D$_2$O) δ 15.4 (CH$_3$), 35.5 (C-2), 44.8, 45.7 (C-1, C-5), 67.0, 72.6 (C-3, C-4) ppm. HRMS (M+Cs$^+$) Calculated 264.0001, found 264.0003.

Compound 13c was reacted with propanol in the presence of DERA to give Compound 13a in 2.1% yield.

$^1$H NMR (D$_2$O) of major anomer: δ 0.87 (d, J=6.7, 3H, CH$_3$ of C-2), 0.93 (d, J=7.4, 3H, CH$_3$ of C-4), 1.38-1.47 (m, 1H, H-2), 1.73 (ddq, J=2.7, 7.4, 14.8, 1H, H-4), 3.40 (m, 1H, H-3 ), 3.42 (dd, J=6.6, 13.3, 1H, H-7), 3.47 (dd, J=3.6, 13.3, 1H, H-7), 3.81 (ddd, J=3.6, 5.0, 6.6 , 1H, H-6), 4.66 (d, J=8.7, 1H, H-1), 4.76 (m, 1H, H-5). $^{13}$C NMR δ 9.1, 9.3 (CH$_3$ of C-4), 11.2, 12.0 (CH$_3$ of C-2), 25.2, 25.3), 38.0, 41.3 (C-2, C-4), 51.7, 51.9 (C-7), 72.0, 71.7 (C-6), 77.4 , 81.8 (C-3), 94.2, 97.1 (C-5), 91.9, 99.6 (C-1).HRMS (M+Cs$^+$) Calcd 364.0273, found 364.0273.

Compound 14a was produced by the DERA-catalyzed condensation of (RS)3-azido-2-hydroxypropanal, prepared as above, and acetaldehyde. Resulting Compound 13a was recovered and hydrogenated over Pd/C as described before to provide Compound 14a.

Compound 14a: $^1$H-NMR (D$_2$O) δ 1.51 (2H, m, H-2), 2.55 (1H, ddd, J=13.1, 7.6, 4.8, H-1), 2.67 (1H, dd, J=13.4, 3.0, H-5), 2.90 (1H, dd, J=13.4, 5.7, H-5), 2.86-2.96 (1H, m, H-1), 3.67 (1H, dt, J=5.9, 2.5, H-4), 3.74 (1H, ddd, J=7.6, 4.6, 3.0, H-3)ppm; $^{13}$C-NMR (D$_2$O) δ 29.9 (C-2), 41.9 (C-1), 48.1 (C-5), 68.8, 69.3 (C-3, C-4) ppm. HRMS (M+): Calculated: 117.0790, found 117.0785.

Example 10. 1,6-Dideoxyidojirimycin; Compound 11

Compound 11 is prepared in a manner similar to that used for the preparation of Compound 6 (Example 6) except that (S)-3-azido-2-hydroxypropanal is utilized with DHAP and rhamnulose-1-phosphate aldolase.

Example 11. Cis-2,3-epoxy-1,4-butane-diol; Compound VI)

Cis-2,3-epoxy-1,4-butane-diol, Compound XXXI, was prepared from 1,4-dihydroxy-2-butene (Compound XXX) according to the reported procedure [Nelson et al., *J. Med. Chem.* 1976, 22, 153] except that the reaction was carried out at room temperature for 36 hours.

Example 12. 2-Azido-2-deoxy-threitol; Compound VII

A solution containing Compound XXXI (1.82 grams, 17.50 millimoles), sodium azide (NaN$_3$; 5.68 grams, 5 equivalents), and ammonium chloride (NH$_4$Cl; 4.68 grams, 5 equivalents) in 100 milliliters (mL) methanol and 12 mL H$_2$O was heated at reflux for 24 hours. The solvent was removed under reduced pressure, then ethanol was added and the precipitate was filtered off. The precipitation procedure was repeated several times to remove excess NaN$_3$ and NH$_4$Cl, to thereby obtain 2-azido-2-deoxy-threitol, Compound XXXII, as yellow liquid (90 percent): R$_f$=0.28 (EtOAc 100 percent); infrared (neat) 2109 cm$^{-1}$ (—N$_3$); $^1$H-NMR (CD$_3$COCD$_3$) δ 3.49 (1H, m) 3.59 (3H, m), 3.79 (5H, m), 4.03 (1H, t, J=5.5 Hz), 4.19 (1H, d, J=5.5), 4.30 (1H, t, J=5.5 Hz) ppm. HRMS (M+H+) calculated 148.0722, found 148.072.

Example 13. 5-Azido-5-deoxy-L-xylo-hexulose-1-phosphate; Compound 24

A solution containing Compound XXXII prepared above (476 milligrams, 3.24 millimoles) in 10 mL H$_2$O was cooled to zero degrees C. and sodium periodate (NaIO$_4$; 762 milligrams, 1.1 equivalent) was added. After 10 minutes, the starting material disappeared completely and a new spot appeared according to thin layer chromatography (Rf=0.5, ethyl acetate). Barium chloride (BaCl$_2$.2H$_2$O; 870 milligrams, 1.1 equivalent) was then added to the solution and the precipitate was filtered off. The solution was acidified to pH 1 with Dowex 50 (H+). Racemic Compound XXXIII, 2-azido-3-hydroxypropionaldehyde, thus prepared was not isolated.

After filtration, the solution containing Compound XXXIII containing Compound 7 was adjusted to pH 7 with sodium hydroxide (NAOH; 10 normal). DHAP (1.5 millimoles) was then added and the solution was readjusted to pH 7 with 10 normal NAOH. To that solution, rabbit muscle FDP aldolase (500 units) was added and the solution was stirred slowly for two days. Enzymatic assay indicated that all of the DHAP had been consumed. Compound 24 was first isolated as the barium salt by adding two equivalents BaCl.2H$_2$O to the reaction mixture. The solution was maintained at −20° C. overnight (about 18 hours). The precipitate was recovered, and treated with Dowex 50 (H+) in distilled water to remove barium cations. After filtration, the solution was adjusted to pH 7 and lyophilized to obtain Compound 24 (75 percent). $^1$H-NMR (D$_2$O) δ 3.13 (1H, d, J=9.5 Hz, H-3), 3.14 (1H, ddd, J-9.5, 5, 11 Hz, H-5), 3.20 (1H, t, J=11 Hz, H-6a), 3.31 (1H, t, J=9.5 Hz, H-4), 3.37 (1H, dd, J=6, 11 Hz, H-6e), 3.40-3.44 (2H, m, 2×H-1) ppm. $^{13}$C-NMR (D$_2$O) δ 61.78, 63.36, 67.35, 70.95, 97.67 (d, J=9.5 Hz) ppm. HRMS (M-4H+ +5Na+) calculated 395.9540, found: 395.9538.

Example 14. (2R)-Methyl-(5S)-hydroxymethyl-(3R,4R)-dihydroxypyrollidine; (2,5,6-Trideoxy-2.5-imino-D-fructose) Compound 25

A solution of Compound 24 (100 milligrams, 0.35 millimoles) in 5 mL water was hydrogenated with 20 milligrams 10 percent palladium/carbon (Pd/C) under 40 pounds per square inch (psi) of hydrogen for one day. The catalyst was removed by filtration and the filtrate was concentrated in vacuo. The residue was chromatographed on silica gel column (methanol: chloroform:H$_2$O=6:4:2) to yield Compound 25 (40 milligrams, 78 percent yield, 2R:2S≈6:1). $^1$H-NMR (D$_2$O) δ 1.31 (3H, d, J-7 Hz, 2R-CH$_3$), 1.27 (3H, d, J-6.5 Hz, 2S-CH$_3$), 3.36 (1H, la, H-2), 3.66 (1H, 2, H-5), 3.74~3.81 (2H, m, 2×H-5), 3.85 (1H, 2, H-3), 4.08 (1H, dd, J=2.5; 4.5 Hz, H-4) $^{13}$C-NMR (D$_2$O) δ 16.58 (C-2'), 57.90 (C-5'), 61.50, 63.44, 75.62, 87.09 ppm. HRMS (M+H+) calculated 148.0974, found 148.0974.

Example 15. Glucosidase, Mannosidase and Galactosidase Inhibition Studies

A. Inhibition Analysis

With these omega-deoxy-azasugars in hand, studies were designed to determine the inhibition kinetics and the results are summarized in Table 1. All the inhibition kinetics are competitive at pH 6.5. Since various N-alkyl derivatives of azasugars were shown to have different inhibition properties [Karpas et al., *Proc. Natl. Acad. Sci.* 1988, 85, 9229], Compound 17 was included in the study. Compound 18 was thought to be a more potent inhibitor than the corresponding precursor Compound 17 because of its zwitterionic character, which may have a stronger electrostatic interaction with the putative active site carboxylate and carboxylic acid residues of glycosidases [Sinnott, in *Enzyme Mechanisms*; Pike et al., Eds., Royal Soc. Chem. London 1987, 259; Lalegerie et al., *Biochemic* 1982, 64, 977; Withers et al., *J. Am. Chem. Soc.* 1988, 1100, 8551; Withers et al., J. Am. Chem. Soc. 1990, 112, 5887]. Kinetic analysis indicates, however, that Compound 18 is a less potent inhibitor than Compound 17 for β-glucosidase from sweet almond by an order of magnitude, although it is similar to Compound 17 for the inhibition of α-glucosidase from brewers yeast. It appears that addition of an oxygen atom to N in the N-oxide perturbs the binding to the enzyme, resulting in a weaker complex, as is also seen with N-methyl 1-deoxynojirimycin N-oxide (Compound 22). For in vivo inhibition, N-alkylation, however, may facilitate transport of the inhibitor across the cell membrane, thereby increasing the effectiveness of the inhibition [Walker et al., *Proc. Natl. Acad. Sci*, 1987, 84, 8120].

Comparison of the K$_i$ values between Compound 17 and Compound 19 (N-methyl 1-deoxynojirimycin) prepared by reductive methylation of 1-deoxynojirimycin [Pederson et al., *Heterocycles* 1989, 28, 477), and that between Compound 23 (1-deoxynojirimycin) and Compound 3c indicates that the 6-OH group is important for binding, presumably through an interaction with a hydrogen-bond acceptor.

B. Inhibition Study

Materials: All of the buffers, enzymes, and substrates were purchased from Sigma and used as received. These included piperazine-N,N'-bis(2-ethanesulfonic acid) (PIPES), sodium acetate (NaOAc), ethylenediaminetetraacetic acid (EDTA), β-D-glucosidase (from sweet almond), p-nitrophenyl β-D-glucoside, α-D-glucosidase, p-nitrophenyl α-D-glucoside, β-N-acetyl-D-glucosaminedase, p-nitrophenyl β-N-acetyl-D-glucosaminide, α-D-mannosidase, and p-nitrophenyl α-D-mannoside.

C. Preparation of solutions:

a) PIPES buffer (0.05M with 0.01 mM EDTA, pH 6.5): To 1 liter (L) deionized $H_2O$ were added 15.1 g PIPES and 35.7 mg EDTA. The pH was adjusted to 6.5 with NaOH (10M).

b) PIPES-NaOAc buffer (0.01M PIPES, 0.2M NaOAc and 0.01 mM EDTA, pH 6.5). This buffer was prepared according to the literature procedure [Dale et al., *Biochemistry* 1985, 24, 3530].

c) β-D-Glucosidase: The stock enzyme solution was prepared by dissolving 15 mg of solid protein (4 units/mg) in 1 mL PIPES-NaOAc buffer solution. This stock enzyme solution was diluted 5-fold for the enzymatic assay.

d) α-D-Glucosidase: 1.5 mg of solid protein (70 units/mg) were dissolved in 1 mL PIPES-NaOAc buffer solution and used for assays without further dilution.

e) β-N-Acetyl-D-Glucosaminedase: 25 units of the protein were suspended in 0.55 mL of 3.2M ammonium sulfate [$(NH_4)_2SO_4$] solution as distributed by Sigma.

f) α-D-Mannosidase: 5 mg of the solid protein were suspended in 1 mL of 3.0M $(NH_4)_2SO_4$ and 0.1 zinc acetate (ZnOAc), as distributed by Sigma.

g) Substrate solutions: all substrates were dissolved in the corresponding buffer solution for enzymatic assay.

D. General Procedure for Enzyme Assay

For each inhibitor, five inhibitor concentrations, ranging from zero to three times $K_i$, were generally used to determine the $K_i$ value. At each inhibitor concentration, six substrate concentrations, spanning from 0.4 $K_m$ to 4 $K_m$, were used to obtain a single Lineweaver-Burk plot. The amount of enzyme added in each assay was adjusted so that less than 10 percent of the substrate, with its lowest substrate concentration, would be consumed within 45 seconds. Since all of the substrates have p-nitrophenol as leaving group, the assays were monitored at 400 nanometers (nm), where the molecular extinction coefficient, ε, was calibrated to be $3204.5 M^{-1} cm^{-1}$ at pH 6.5. The following illustrates the detailed procedure.

To a 1 mL disposable cuvette were added 950 microliters (μL) of the NaOAc-PIPES buffer solution, 20 μL of the inhibitor solution and 20 μL of the p-nitrophenyl β-D-glucoside solution (100 Mm in PIPES-NaoAc buffer, PH 6.5). The solution was well mixed and 20 μL of the β-D-glucosidase solution were injected into the cuvette to start the reaction. The reaction was monitored at 400 nm on a Beckman DU-70 photospectrometer for 45 seconds and the initial hydrolysis rate was calculated. The same procedure was repeated with five other substrate concentrations. After all the initial rates were accumulated, the corresponding Lineweaver-Burk plot at that inhibitor concentration was constructed.

PIPES-NaOAc buffer was used for all the enzymes except β-N-acetyl-D-glucosaminedase, for which PIPES buffer was used.

Exemplary $K_i$ data are provided in Table 1, below.

TABLE 1

| | Glycosidase Inhibition | |
|---|---|---|
| Compound | Brewer's Yeast (BY) or Sweet Almond (SA) | $K_i(M)$ |
| 3c | α-Glucosidase (BY) | $1.56 \times 10^{-3}$ |
| | β-Glucosidase (SA) | $7.8 \times 10^{-4}$ |
| 17 | α-Glucosidase (BY) | $1.78 \times 10^{-3}$ |
| | β-Glucosidase (SA) | $1.4 \times 10^{-4}$ |
| 18 | α-Glucosidase (BY) | $6.95 \times 10^{-3}$ |
| | β-Glucosidase (SA) | $1.49 \times 10^{-3}$ |
| | Controls | |
| 19 | α-Glucosidase (BY) | $3.69 \times 10^{-4}$ |
| | Type I (calf liver) | $7.0 \times 10^{-8}$ |
| | β-Glucosidase (SA) | $4.3 \times 10^{-5}$ |
| 22 | α-Glucosidase (BY) | $>1.0 \times 10^{-2a}$ |
| | β-Glucosidase (SA) | $8.0 \times 10^{-5}$ |
| 23 | α-Glucosidase (BY) | $8.67 \times 10^{-6}$ |
| | Type I (calf liver) | $1.0 \times 10^{-6a}$ |
| | β-Glucosidase (SA) | $1.8 \times 10^{-5b}$ |
| | α-D-Mannosidase (jack bean) | $4.0 \times 10^{-4}$ |
| | β-D-Galactosidase (jack bean) | No inhibition[c] |

[a]Schweden et al., Arch. Biochem. Biophys., 1986, 248, 335
[b]Dale et al., Biochemistry, 1985, 24, 3530
[c]No significant inhibition observed with 10 mM inhibitor in the assay.

Example 16 Fucosidase Inhibition Studies

Previous studies with fucosidase have implicated the involvement of two carboxylate catalytic groups in the hydrolysis of p-nitrophenyl-α-L-fucoside (fuc-pNP) with a general acid-base mechanism. Lipshutz et al., *J. Am. Chem. Soc.*, 104:2305 (1982). Hydrolysis occurs with retention of configuration, suggesting a double displacement mechanism or a directed hydroxyl attack with a oxocarbonium ion mechanism as has been proposed for many of the other stereochemistry retaining glycosidases. See. e.g., Ho, T.-L., "Hard and Soft Acids and Bases Principles in organic Chemistry", Academic Press, New York (1977); and Pederson et al., *Tetrahedron Lett.*, 47:2643 (1991).

Fucose is a competitive inhibitor versus fuc-pNP ($K_i = 0.30 \pm 0.01$ mM) and phenol, used as an analog of p-nitrophenol, is a noncompetitive inhibitor ($K_{ii} = 112 \pm 16$ mM and $K_{is} = 0.18 \pm 0.02$ mM). The kinetic mechanism implicated from these experiments is uni-bi sequential ordered with p-nitrophenol being released first and fucose released second.

α-L-Fucosidase activity was measured by incubating the enzyme (0.005 Units) with fuc-pNP (0.2–2.0 μM) in 0.4 ml of 50 mM acetate buffer, pH 5.5 for 20 minutes at 25° C. in the absence and presence of the azasugars of the present invention. The reaction was stopped by the addition of 0.8 ml of 2 Mm glycine buffer, pH 10.5. The amount of formed p-nitrophenol was determined by optical density spectroscopy at a wavelength of 400 nm. Exemplary $K_i$ data are shown below in Table 2.

TABLE 2

| α-L-Fucosidase Inhibition | |
|---|---|
| Compound | $K_i$(mM) |
| 3c | 1.7 ± 0.3 |
| 6 | 1.0 ± 0.1 |
| 11 | 7.9 ± 0.9 |
| 3a | 0.01 ± 0.001 |
| 124 | 0.05 ± 0.006 |
| L-1-deoxyfuconojirimycin | $1 \times 10^{-5}$ |
| D-1-deoxymannojirimycin | 0.03 ± 0.01 |
| L-Fucose | 0.30 ± 0.10 |

Example 17 Preparation of DERA.

All steps were carried out at 4° C. with the exception of FPLC which was performed at room temperature. A total of 6L of *E. coli* DH5a containing pVH17 was grown at 37° C. with agitation. The cells were cooled to 4° C. and harvested by centrifugation at 8K for 20 minutes. The cells (about 72 g) were resuspended in 200 mL of buffer containing 100 mM TRIS pH 7.6 and 2 mM EDTA (buffer A). The cells were lysed in a French Pressure apparatus (Aminco, Inc.) and centrifuged at 16,000×g for 30 minutes. The supernatant fluid was decanted and made 1% with streptomycin sulfate with stirring over a period of 20 min. The resulting solution was centrifuged as before. The resulting supernatant fluid cut was with ammonium sulfate (40–60%), and the resulting pellet was resuspended in buffer A. This solution was dialyzed extensively against buffer A. One tenth of this solution was used for further purification, whereas the remaining solution was lyophilized and stored at −70° C. Further purification was achieved by FPLC with a MonoQ 10/10 anion exchange column. The sample-was eluted with a gradient of 50 Mm NaCl in buffer A. The enzymatically active fractions were pooled and applied to a phenyl sepharose FPLC column in buffer A containing 40 mM NaCl. Under these conditions, the remaining contaminating proteins stick to phenyl sepharose while DERA elutes in the void volume.

Example 18: D-1-deoxytalonojirimycin; (Compound 124)

DHAP (0.5 mmole) was added to an aqueous solution of (R)-3-azido-2-hydroxypropanal (1 mmole in 40 ml) and the pH value adjusted to 7.0 with 10N NaOH. To this solution was added fuculose-1-phosphate aldolase from *E. coli* (4 g), which had been treated with egg white lysozyme (40 mg) in Tris buffer (pH 7.5, 25 ml) for 1 hour at 35° C., to form a mixture and the mixture stirred slowly for 2 days. The stirred mixture was adjusted to a pH value of 4.7, and acid phosphatase (400 units) added. The resulting mixture was incubated at 37° C. for 48 hours, neutralized to a pH value of 7.0 and lyophilized. The residue was treated with MEOH and filtered to remove the insoluble material. The MEOH was removed under reduced pressure and the crude product purified with silica gel column chromatography ($CHCl_3$:MeOH=6:1) to give 6-azido-6-deoxy-D-xylo-hexulose in 30% yield.

6-Azido-6-deoxy-D-xylo-hexulose (10 mg, 0.048 mmole) prepared above was hydrogenated with 10% Pd/C under 45 psi of hydrogen for 1 day in 10 ml of water. The catalyst was removed by filtration and the filtrate concentrated in vacuo and further purified with a Biogel P2 column to give Compound 124 in 67% yield (5 mg).

Example 19: Reductive Alkylation of Azasugars

About 4 equivalents of an aldehyde (formaldehyde, butanal or phenylacetaldehyde, for example) are added to 10 ml MEOH containing about 10 mg (0.06 mmole) of an azasugar of the present invention and 10 mg of 10% Pd/C to form a mixture. The mixture is hydrogenated under 50 psi of hydrogen for 24 hours. The catalyst is filtered off and the solvent is removed under reduced pressure. The residue is purified with silica gel column chromatography to give N-alkyl derivatives of the azasugars in good yield.

The foregoing is intended as illustrative of the present invention but not limiting. Numerous variations and modifications may be effected without departing from the true spirit and scope of the novel concepts of the invention.

We claim:

1. A process of forming a 1,5-dideoxy-azafuranose or 1,6-dideoxy-azapyranose which comprises the step of reductively cyclizing an azido-substituted α-ketose phosphate compound having a five- or six-carbon chain by hydrogenation in the presence of a palladium catalyst, the carbon atom of the azido substituent and the carbon of the keto group being separated in the chain by two or three carbon atoms.

2. The process according to claim 1 wherein the α-ketose phosphate compound contains a six-carbon chain and includes a substituent in place of a ketose hydroxyl group selected from the group consisting of halide, $C_1$–$C_4$ alkoxy and $NR^6R^7$ where $R^6$ is hydrogen or $C_1$–$C_4$ alkyl and $R^7$ is hydrogen, $C_1$–$C_4$ alkyl, $C_1$–$C_4$ acyl or $NR^6R^7$ together form a cyclic amido group that contains 4–8 carbon atoms.

3. The process according to claim 1 wherein the six-carbon α-ketose phosphate contains a hydroxyl group substituent on each carbon atom that separates the carbon of the keto group and the carbon of the azido substituent.

4. The process according to claim 1 including the further step of recovering the reductively cyclized hydrogenation product.

5. The process according to claim 1 wherein said α-ketose phosphate compound has the structure

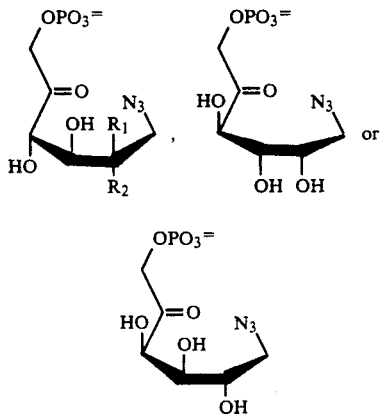

a: $R_1$ = OH, $R_2$ = H
b: $R_1$ = AcNH, $R_2$ = H
c: $R_1$ = H, $R_2$ = OH
d: $R_1$ = H, $R_2$ = AcNH
e: $R_1$ = F, $R_2$ = H
f: $R_1$ = OEt, $R_2$ = H wherein $R_1$ and $R_2$ are as shown in a through f.

6. The process according to claim 1 wherein a 1,6-dideoxy-azapyranose is formed.

7. The process according to claim 6 wherein said 1,6-dideoxy-azapyranose has a structure represented by formula III, below

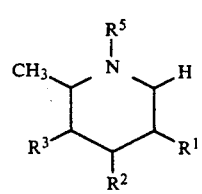

III wherein R¹ is hydroxyl, $C_1$-$C_4$ alkoxy, halide, or $NR^6R^7$ where $R^6$ is hydrogen or $C_1$-$C_4$ alkyl and $R^7$ is hydrogen, $C_1$-$C_4$ alkyl, $C_1$-$C_4$ acyl; or $NR^6R^7$ together form a cyclic imido group that contains 4–8 carbon atoms;

$R^2$ is hydrogen or hydroxyl;

$R^3$ is hydrogen or hydroxyl; and $R^5$ is hydrogen.

8. The process according to claim 7 wherein each of $R^2$ and $R^3$ is hydroxyl.

9. The process according to claim 8 wherein $R^1$ is hydroxyl.

10. The process according to claim 6 wherein said 1,6-dideoxy-azapyranose has the formula

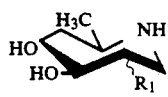

wherein R₁ is selected from the group consisting of hydroxyl, N-acetyl, fluoro and ethoxy.

11. A process of forming a 1,6-dideoxy-azapyranose which comprises the step of reductively cyclizing an azido-substituted α-ketose phosphate compound having a six-carbon chain by hydrogenation in the presence of a palladium catalyst, the carbon atom of the azido substituent and the carbon atom of the keto group being separated in the chain by three carbon atoms.

12. The process according to claim 11, wherein the formed 1,6-dideoxy-azapyranose has a structure selected from

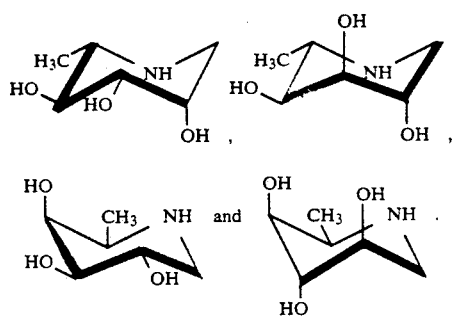

13. The process according to claim 11 including the further step of recovering the reductively cyclized hydrogenation product.

14. A process for forming a 1,omega-dimethyl-azafuranose which comprises the step of reductively cyclizing an azido-substituted α-ketose phosphate compound having a six-carbon chain by hydrogenation in the presence of a palladium catalyst, the carbon atom of the azido substituent and the carbon atom of the keto group being separated by three carbon atoms.

15. The process according to claim 14 wherein the formed 1,omega-dimethyl-azafuranose has a formula selected from

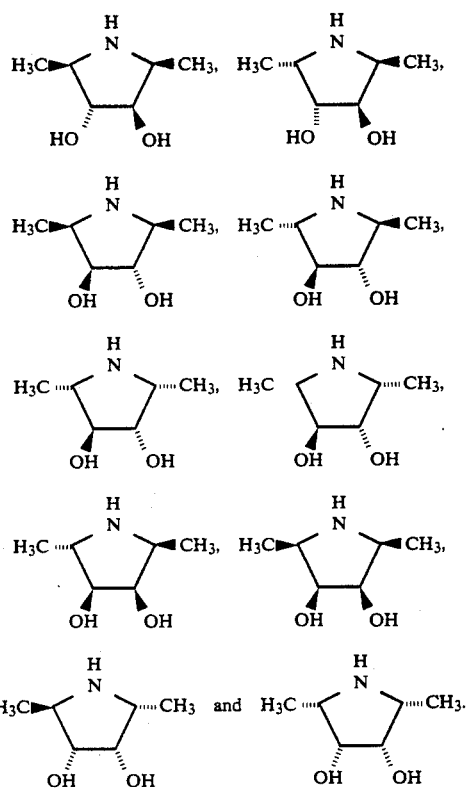

16. The process according to claim 14 including the further step of recovering the reductively cyclized hydrogenation product.

* * * * *